United States Patent
Wussow et al.

(10) Patent No.: US 11,844,833 B2
(45) Date of Patent: *Dec. 19, 2023

(54) EXPRESSION SYSTEM FOR EXPRESSING HERPESVIRUS GLYCOPROTEIN COMPLEXES

(71) Applicant: CITY OF HOPE, Duarte, CA (US)

(72) Inventors: Felix Wussow, Monrovia, CA (US); Don J. Diamond, Glendora, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/806,157

(22) Filed: Jun. 9, 2022

(65) Prior Publication Data

US 2023/0140549 A1 May 4, 2023

Related U.S. Application Data

(63) Continuation of application No. 16/630,624, filed as application No. PCT/US2018/042046 on Jul. 13, 2018, now Pat. No. 11,389,529.

(60) Provisional application No. 62/532,298, filed on Jul. 13, 2017.

(51) Int. Cl.
*A61K 39/245* (2006.01)
*C07K 14/045* (2006.01)
*C07K 14/05* (2006.01)

(52) U.S. Cl.
CPC .......... *A61K 39/245* (2013.01); *C07K 14/045* (2013.01); *C07K 14/05* (2013.01)

(58) Field of Classification Search
CPC ...... A61K 39/245; A61K 39/00; A61K 39/12; C07K 14/045; C07K 14/05; C07K 14/03; C07K 14/005; A61P 31/22; C12N 2800/50; C12N 15/86; C12N 2710/16022; C12N 2710/16122; C12N 2710/24143; C12N 2800/204; C12N 2800/30; C12N 2840/206
See application file for complete search history.

(56) References Cited

U.S. PATENT DOCUMENTS

| | | |
|---|---|---|
| 2014/0030292 A1 | 1/2014 | Franti et al. |
| 2014/0127247 A1 | 5/2014 | Dubensky et al. |
| 2014/0302530 A1 | 10/2014 | Picker et al. |
| 2015/0216965 A1 | 8/2015 | Diamond et al. |
| 2021/0163542 A1 | 6/2021 | Cui et al. |

FOREIGN PATENT DOCUMENTS

| | | |
|---|---|---|
| WO | 2014/018117 A1 | 1/2014 |
| WO | 2016/116905 A1 | 7/2016 |

OTHER PUBLICATIONS

Gaskell R, Dawson S, Radford A, Thiry E. Feline herpesvirus. Vet Res. Mar.-Apr. 2007;38(2):337-54. doi: 10.1051/vetres:2006063. Epub Feb. 13, 2007. PMID: 17296160. (Year: 2007).*
Small JC, Ertl HC. Viruses—from pathogens to vaccine carriers. Curr Opin Virol. Oct. 2011;1(4):241-5. doi: 10.1016/j.coviro.2011.07.009. PMID: 22003377; PMCID: PMC3190199. (Year: 2011).*
Adler, B., et al., "Role of human cytomegalovirus UL131A n cell type-specific virus entry and release," J. Gen. Virol. 87:2451-2460 (2006).
Andreoni, M., et al., "A rapid microneutralization assay for the measurement of neutralizing antibody reactive with human cytomegalovirus," J. Virol. Meth. 23:157-168 (1989).
Bernstein, D. I., et al., "Safety and efficacy of a cytomegalovirus glycoprotein B (GB) vaccine in adolescent girls a randomized clinical trial," Vaccine 34(3):313-319 (2016).
Birnboim, H.C., et al., "A rapid alkaline extraction procedure for screening recombinant plasmid DNA," Nucl. Acids Res. 7(6):1513-1523 (1979).
Butler, D., et al., "Zika raises wider birth-defect issue," Nature 535:17 (2016).
Carroll, M. W., et al., "Host range and cytopathogenicity of the highly attenuated MVA strain of vaccinia virus: Propagation and generation of recombinant viruses in a nonhuman mammalian cell line," Virol. 238:198-211 (1997).
Chiuppesi, F., et al., "Vaccine-derived neutralizing antibodies to the human cytomegalovirus gH/gL pentamer potently block primary cytotrophoblast infection," J. Virol. 89(23):11884-11898 (2015).
Cottingham, M. G., et al., "Recombinant-mediated genetic engineering of a bacterial artificial chromosome clone of modified vaccinia virus ankara (MVA)," Plos One 3(2):e1638 (2008).
Cottingham, M. G., et al., "Rapid generation of markerless recombinant MVA vaccines by en passant recombineering of a self-excising bacterial artificial chromosome," J. Virol.Meth. 168:233-236 (2010).
Cottingham, M. G., et al., "Recombinant MVA vaccines: dispelling the myths," Vaccine 31:4247-4251 (2013).
Cui, X.,et al., "Cytomegalovirus vaccines fail to induce epithelial entry neutralizing antibodies comparable to natural infection," Vaccine 26(45):5760-5766 (2008).
De Felipe, P., "Skipping the co-expression problem: the new 2A "Chysel" technology," Genetic Vaccines and Therapy 2:13 (2004).
Domi, A., et al., "Cloning the vaccinia virus genome as a bacterial artificial chromosome in *Escherichia coli* and recovery of infectious virus in mammalian cells," PNAS 99(19):12415-12420 (2002).

(Continued)

*Primary Examiner* — Rachel B Gill
(74) *Attorney, Agent, or Firm* — Perkins Coie LLP; Lara J. Dueppen; Gregory J. Logan

(57) ABSTRACT

An expression system for expressing a herpesvirus glycoprotein complex including a vector inserted with two or more nucleic acid sequences that encode two or more subunits of a herpesvirus glycoprotein complex linked by one or more linking sequences such that the subunits are co-expressed simultaneously and self-processed to assemble into a glycoprotein complex. The expression system or the vector can be included in a vaccine composition. The vaccine composition can be used for preventing or treating herpesvirus infections.

21 Claims, 6 Drawing Sheets

Specification includes a Sequence Listing.

(56) References Cited

OTHER PUBLICATIONS

Donnelly, M. L. L., et al., "Analysis of the aphthovirus 2A/2B polyprotein 'cleavage' mechanism indicates not a proteolytic reaction, but a novel translational effect: a putative ribosomal 'skip'," J. Gen. Virol. 82:1013-1025 (2001).

Draper, S. J., et al., "Utilizing poxviral vectored vaccines for antibody induction—Progress and prospects," Vaccine 31:4223-4230 (2013).

Freed, D. C., et al., "Pentameric complex of viral glycoprotein H is the primary target for potent neutralization by a human cytomegalovirus vaccine," PNAS 110:E4997-E5005 (2013).

Gerna, G., et al., "Human cytomegalovirus serum neutralizing antibodies block virus infection of endothelial/epithelial cells, but not fibroblasts, early during primary infection," J. Gen. Virol. 89:853-865 (2008).

Gerna, G., et al., "Monoclonal antibodies to different components of the human cytomegalovirus (HCMV) pentamer gH/gL/pUL128L and trimer gH/gL/gO as well as antibodies elicited during primary HCMV infection prevent epithelial cell syncytium formation," J. Virol. 90(14):6216-6223 (2016).

Gilbert, S. C., "Clinical development of Modified Vaccinia virus Ankara vaccines," Vaccine 31:4241-4246 (2013).

Hahn, G., et al., "Human cytomegalovirus UL131-128 genes are indispensable for virus growth in endothelial cells and virus transfer to leukocytes," J. Virol. 78(18):10023-10033 (2004).

Hofmann, I., et al., "Expression of the Human Cytomegalovirus Pentamer Complex for vaccine use in a CHO system," Biotechnol. Bioeng. 112:2505-2515 (2015).

Jiang, X. J., et al., "UL74 of human cytomegalovirus contributes to virus release by promoting secondary envelopment of virions," J. Virol. 82(6):2802-2812 (2008).

Kabanova, A., et al., "Antibody-driven design of a human cytomegalovirus gHgLpUL128L subunit vaccine that selectively elicits potent neutralizing antibodies," PNAS 111(5):17965-17970 (2014).

Kim, J. H., et al., "High cleavage efficiency of a 2A peptide derived from porcine teschovirus-1 in human cell lines, zebrafish and mice," PLOS One 6(4):e18556 (2011).

La Rosa, C., et al., "MVA vaccine encoding CMV antigens safely induces durable expansion of CMV-specific T cells in healthy adults," Blood 129(1):114-125 (2017).

Lilleri, D., et al., "Antibodies against neutralization epitopes of human cytomegalovirus gH/gL/pUL128-130-131 complex and virus spreading may correlate with virus control in vivo," J. Clin. Immunol. 32:1324-1331 (2012).

Lilleri, D., et al., "Fetal human cytomegalovirus trasnsmission correlates with delayed maternal antibodies to gH/gL/pUL128-130-131 complex during primary infection," PLOS One 8(3):e59863 (2013).

Liu, D. X., et al., "Identification and expression of the human herpesvirus 6 glycoprotein H and interaction with an accessory 40K glycoprotein," J. Gen. Virol. 74:1847-1857 (1993).

Loomis, R. J., et al., "Vectored co-delivery of human cytomegalovirus gH and gL proteins elicits potent complement-independent neutralizing antibodies," Vaccine 31(6):919-926 (2013).

Loughney, J. W., et al., "Soluble human cytomegalovirus gH/gL/pUL128-131 pentameric complex, but not gH/gL, inhibits viral entry to epithelial cells and presents dominant native neutralizing epitopes," J. Biol. Chem. 290(26):15985-15995 (2015).

Macagno, A., et al., "Isolation of human monoclonal antibodies that potently neutralize human cytomegalovirus infection by targeting different epitopes on the gH/gL/UL128-131A complex," J. Virol. 84(2):1005-1013 (2010).

Manghera, A., et al., "Human Cytomegalovirus Vaccination: Progress and perspectives of recombinant GB," Future Virol. 11(6):439-449 (2016).

Manicklal, S., et al., "The "silent" global burden of congenital cytomegalovirus," Clin. Microbiol. Rev. 26(1):86-102 (2013).

Manuel, E. R., et al., "Intergenic region 3 of modified vaccinia Ankara is a functional site for insert gene expression and allows for potent antigen-specific immune responses," Virol. 403(2):155-162 (2010).

Mayr, A., et al., "[Attenuation of virulent fowl pox virus in tissue culture and characteristics of the attenuated virus]. Zentralblatt fur veterinarmedizin," Reihe B, J. Vet. Med., Series B 13:1-13 (1966).

Meisinger-Henschel, C., et al., "Genomic sequence of chorioallantois vaccinia virus Ankara, the ancestor of modified vaccinia virus Ankara," J. Gen. Virol. 88:3249-3259 (2007).

Meisinger-Henschel, C., et al., "Introduction of the six major genomic deletions of modified vaccinia virus Ankara (MVA) into the parental vaccinia virus is not sufficient to reproduce an MVA-like phenotype in cell culture and in mice," J. Virol. 84(19):9907-9919 (2010).

Mlakar, J., et al., "Zika virus associated with microcephaly," N. Engl. J. Med. 374:951-958 (2016).

Pass, R. F., "Development and evidence for efficacy of CMV glycoprotein B vaccine with MF59 adjuvant," J. Clin. Virol. 46(Suppl. 4):S73-S76 (2009).

Pereira, L., et al., "Intrauterine growth restriction caused by underlying congenital cytomegalovirus infection," J. Infect. Dis. 209:1573-1584 (2014).

Ryan, M. D., et al., "Cleavage of foot-and-mouth disease virus polyprotein is mediated by residues located within a 19 amino acid sequence," J. Gen. Virol. 72:2727-2732 (1991).

Ryckman, B. J., et al., "Human cytomegalovirus entry into epithelial and endothelial cells depends on genes UL128 to UL150 and occurs by endocytosis and low-pH fusion," J. Virol. 80(2):710-722 (2006).

Sampaio, K. L., et al., "Human cytomegalovirus labeled with green fluorescent protein for live analysis of intracellular particle movements," J. Virol. 79(5):2754-2767 (2005).

Schmelz, M., et al., "Assembly of vaccinia virus: the second wrapping cisterna is derived from the trans golgi network," J. Virol. 68(1):130-147 (1994).

Simpson, J. A., et al., "Neutralizing monoclonal antibodies that distinguish three antigenic sites on human cytomegalovirus glycoprotein H have conformationally distinct binding sites," J. Virol. 67(1):489-496 (1993).

Sinzger, C., et al., "Cloning and sequencing of a highly productive, endotheliotropic virus strain derived from human cytomegalovirus TB40/E," J. Gen. Virol. 89:359-368 (2008).

Szymczak, A. L., et al., "Correction of multi-gene deficiency in vivo using a single 'self-cleaving' 2A peptide—based retroviral vector," Nat. Biotechnol. 22(5):589-594 (2004).

Tischer, B. K., et al., "Two-step red-mediated recombination for versatile high-efficiency markerless DNA manipulation in *Escherichia coli*," BioTechniques 40:191-197 (2006).

Tischer, B. K., et al., "A self-excisable infectious bacterial artificial chromosome clone of varicella-zoster virus allows analysis of the essential tegument protein encoded by ORF9," J. Virol. 81(23):13200-13208 (2007).

Tischer, B. K., et al., "En passant mutagenesis: A two step markerless red recombination system," Methods Mol. Biol. 634:421-430 (2010).

Tischer, B. K., et al., "Viral bacterial artificial chromosomes: Generation, mutagenesis, and removal of mini-F sequences," J. Biomed. Biotechnol. 2012:472537 (2012).

United States Patent and Trademark Office, International Search Report and Written Opinion dated Nov. 15, 2018 for International Application No. PCT/US2018/042046.

Vanarsdall, A. L., et al., "Human cytomegalovirus entry into cells," Curr. Opin. Virol. 2(1):37-42 (2012).

Vanarsdall, A. L., et al., "Human cytomegalovirus gH/gL forms a stable complex with the fusion protein GB in virions," PLOS Pathog. 12(4):e1005564 (2016).

Verheust, C., et al., "Biosafety aspects of modified vaccinia virus Ankara (MVA)-based vectors used for gene therapy or vaccination," Vaccine 30:2623-2632 (2012).

Wagner, S., et al., "Rationalizing membrane protein overexpression," Trends Microbiol. 24(8):364-371 (2006).

(56) References Cited

OTHER PUBLICATIONS

Wang, D., et al., "Human cytomegalovirus virion protein complex required for epithelial and endothelial cell tropism," PNAS 102(50):18153-18158 (2005).

Wang, D., et al., "A replication-defective human cytomegalovirus vaccine for prevention of congenital infection," Sci. Transl. Med. 8:362ra145 (2016).

Wang, Z., et al., "Recombinant modified vaccinia virus Ankara expressing a soluble form of glycoprotein B causes durable immunity and neutralizing antibodies against multiple strains of human cytomegalovirus," J. Virol. 78(8):3965-3976 (2004).

Wang, Z., et al., "Modified H5 promoter improves stability of insert genes while maintaining immunogenicity during extended passage of genetically engineered MVA vaccines," Vaccine 28:1547-1557 (2010).

Wen, Y., et al., "Human cytomegalovirus gH/gL/UL128/UL130/UL131A complex elicits potently neutralizing antibodies in mice," Vaccine 32:3796-3804 (2014).

Wille, P. T., et al., "A human cytomegalovirus gO-null mutant fails to incorporate gH/gL into the virion envelope and is unable to enter fibroblasts and epithelial and endothelial cells," J. Virol. 84(5):2585-2596 (2010).

Wussow, F., et al., "Red-mediated transposition and final release of the mini-F vector of a cloned infectious herpesvirus genome," PLOS One 4(12):e8178 (2009).

Wussow, F., et al., "A vaccine based on the Rhesus cytomegalovirus UL128 complex induces broadly neutralizing antibodies in Rhesus Macaques," J. Virol. 87(3):1322-1332 (2013).

Wussow, F., et al., "Human cytomegalovirus vaccine based on the envelope gH/gL pentamer complex," PLOS Pathog. 10(11):e1004524 (2014).

Wussow, F., et al., "Exploiting 2A peptides to elicit potent neutralizing antibodies by a multi-subunit herpesvirus glycoprotein complex," J. Virolog. Meth. 251:30-37 (2018).

Wyatt, L. S., et al., "Elucidating and minimizing the loss by recombinant vaccinia virus of human immunodeficiency virus gene expression resulting from spontaneous mutations and positive selection," J. Virol. 83(14):7176-7184 (2009).

Zhou, M., et al., "Human cytomegalovirus gH/gL/gO promotes the fusion step of entry into all cell types, whereas gH/gL/UL128-131 broadens virus tropism through a distinct mechanism," J. Virol. 89(17):8999-9009 (2015).

\* cited by examiner

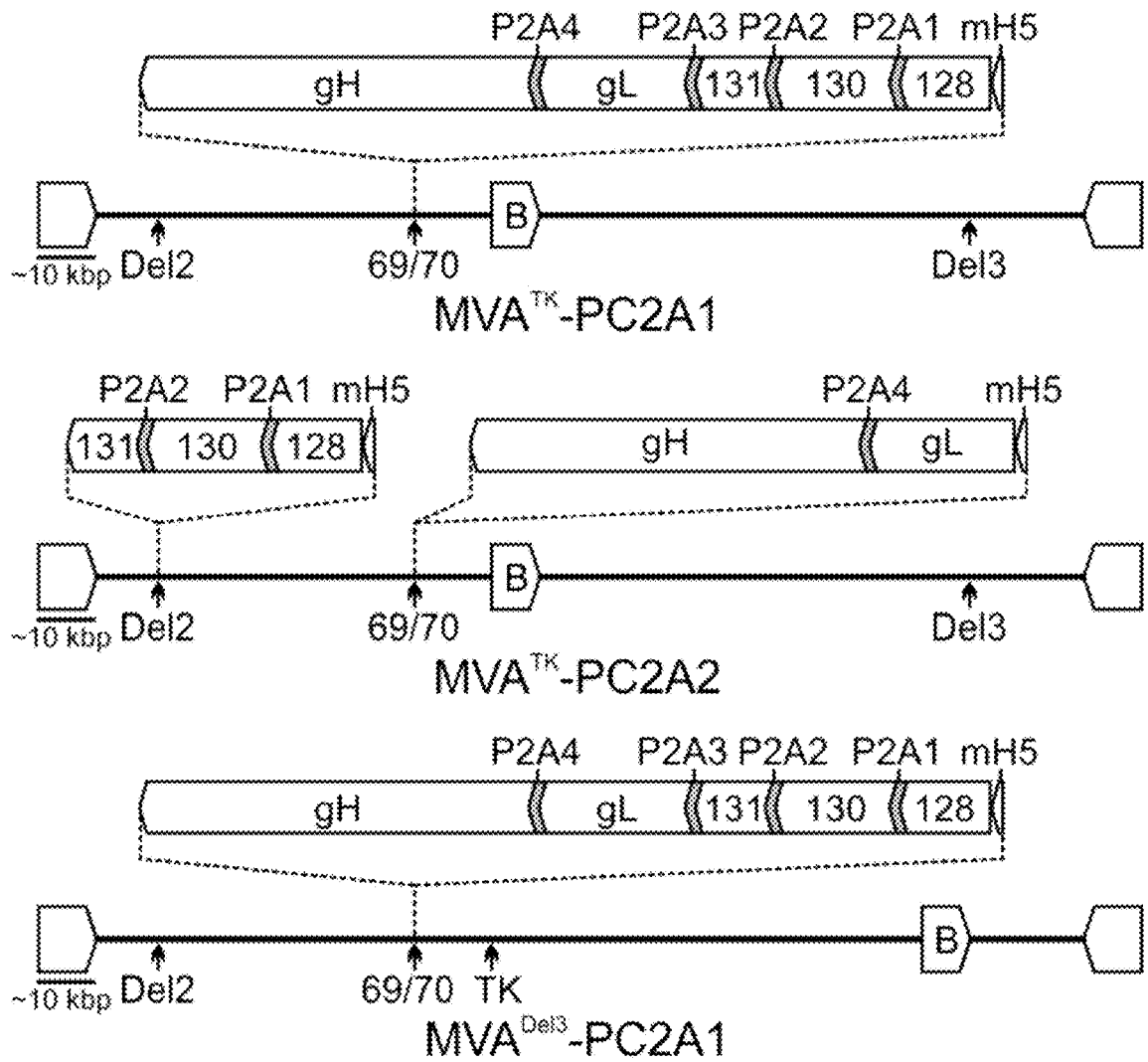

SEQUENCE LISTING

```
<160> NUMBER OF SEQ ID NOS: 38

<210> SEQ ID NO 1
<211> LENGTH: 22
<212> TYPE: PRT
<213> ORGANISM: Artificial Sequence
<220> FEATURE:
<223> OTHER INFORMATION: P2A peptide

<400> SEQUENCE: 1

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 2
<211> LENGTH: 66
<212> TYPE: DNA
<213> ORGANISM: Artificial Sequence
<220> FEATURE:
<223> OTHER INFORMATION: P2A1 peptide

<400> SEQUENCE: 2
ggatcgggag cgactaactt ctcattgttg aaacaggcag gagatgtcga agagaaccct      60
ggtcca                                                                66

<210> SEQ ID NO 3
<211> LENGTH: 66
<212> TYPE: DNA
<213> ORGANISM: Artificial Sequence
<220> FEATURE:
<223> OTHER INFORMATION: P2A2 peptide

<400> SEQUENCE: 3
ggttccggtg caacgaattt ctcccttcta aagcaagccg gtgacgtgga ggagaatccc      60
ggaccc                                                                66

<210> SEQ ID NO 4
<211> LENGTH: 66
<212> TYPE: DNA
<213> ORGANISM: Artificial Sequence
<220> FEATURE:
<223> OTHER INFORMATION: P2A3 peptide

<400> SEQUENCE: 4
ggtagtggtg ccaccaattt ctcgttactt aaacaagcgg gtgacgttga agagaatccg      60
ggacct                                                                66

<210> SEQ ID NO 5
<211> LENGTH: 66
```

```
<212> TYPE: DNA
<213> ORGANISM: Artificial Sequence
<220> FEATURE:
<223> OTHER INFORMATION: P2A4 peptide

<400> SEQUENCE: 5
ggatcaggag ctacaaactt tagtctatta aagcaggctg agatgtaga ggagaaccca      60 ggtccg                                                                66

<210> SEQ ID NO 6
<211> LENGTH: 7
<212> TYPE: DNA
<213> ORGANISM: Artificial Sequence
<220> FEATURE:
<223> OTHER INFORMATION: vaccinia transcription termination signal

<400> SEQUENCE: 6 tttttat                                                                7

<210> SEQ ID NO 7
<211> LENGTH: 73
<212> TYPE: DNA
<213> ORGANISM: Artificial Sequence
<220> FEATURE:
<223> OTHER INFORMATION: forward primer

<400> SEQUENCE: 7
aaaaaatata ttatttttat gttattttgt taaaaataat catcgaatac gaactagtat      60
aaaaaggcgc gcc                                                        73

<210> SEQ ID NO 8
<211> LENGTH: 77
<212> TYPE: DNA
<213> ORGANISM: Artificial Sequence
<220> FEATURE:
<223> OTHER INFORMATION: reverse primer

<400> SEQUENCE: 8
gaagatacca aatagtaaa gattttgcta ttcagtggac tggatgattc aaaaattgaa       60
aataaataca aaggttc                                                    77

<210> SEQ ID NO 9
<211> LENGTH: 84
<212> TYPE: DNA
<213> ORGANISM: Artificial Sequence
<220> FEATURE:
<223> OTHER INFORMATION: forward primer

<400> SEQUENCE: 9
aattgtactt tgtaatataa tgatatatat tttcacttta tctcatttga tttttataaa      60
aattgaaaat aaatacaaag gttc                                            84

<210> SEQ ID NO 10
<211> LENGTH: 70
<212> TYPE: DNA
<213> ORGANISM: Artificial Sequence
<220> FEATURE:
<223> OTHER INFORMATION: reverse primer

<400> SEQUENCE: 10
attccgaaat ctgtacatca tgcagtggtt aaacaaaaac attttattc ctagtataaa       60 aaggcgcgcc                                                            70
```

<210> SEQ ID NO 11
<211> LENGTH: 80
<212> TYPE: DNA
<213> ORGANISM: Artificial Sequence
<220> FEATURE:
<223> OTHER INFORMATION: forward primer

<400> SEQUENCE: 11
atatgaatat gatttcagat actatatttg ttcctgtaga taataactaa aaattttttat    60 ctagtataaa aaggcgcgcc    80

<210> SEQ ID NO 12
<211> LENGTH: 80
<212> TYPE: DNA
<213> ORGANISM: Artificial Sequence
<220> FEATURE:
<223> OTHER INFORMATION: reverse primer

<400> SEQUENCE: 12
ggaaaatttt tcatctctaa aaaaagatgt ggtcattaga gtttgatttt tataaaaatt    60
gaaaataaat acaaaggttc    80

<210> SEQ ID NO 13
<211> LENGTH: 79
<212> TYPE: DNA
<213> ORGANISM: Artificial Sequence
<220> FEATURE:
<223> OTHER INFORMATION: forward primer

<400> SEQUENCE: 13
ttggggaaat atgaacctga catgattaag attgctcttt cggtggctgg taaaaaattg    60
aaaataaata caaaggttc    79

<210> SEQ ID NO 14
<211> LENGTH: 70
<212> TYPE: DNA
<213> ORGANISM: Artificial Sequence
<220> FEATURE:
<223> OTHER INFORMATION: reverse primer

<400> SEQUENCE: 14
acaaaattat gtattttgtt ctatcaacta cctataaaac tttccaaata ctagtataaa    60
aaggcgcgcc    70

<210> SEQ ID NO 15
<211> LENGTH: 80
<212> TYPE: DNA
<213> ORGANISM: Artificial Sequence
<220> FEATURE:
<223> OTHER INFORMATION: forward primer

<400> SEQUENCE: 15
ggtttattgg attcgtgtaa tcatatattt tgcataacat gcatcatttt tataaaaatt    60
gaaaataaat acaaaggttc    80

<210> SEQ ID NO 16
<211> LENGTH: 77
<212> TYPE: DNA
<213> ORGANISM: Artificial Sequence
<220> FEATURE:
<223> OTHER INFORMATION: reverse primer

<400> SEQUENCE: 16

```
acaattatcc gacgcaccgg tttctcttcg tgttctatgc catatattga tttttatcta    60
gtataaaaag gcgcgcc                                                   77

<210> SEQ ID NO 17
<211> LENGTH: 77
<212> TYPE: DNA
<213> ORGANISM: Artificial Sequence
<220> FEATURE:
<223> OTHER INFORMATION: forward primer

<400> SEQUENCE: 17
gaatatgact aaaccgatga ccatttaaaa acccctctct agctttcact aaaaattgaa    60
aataaataca aaggttc                                                   77

<210> SEQ ID NO 18
<211> LENGTH: 70
<212> TYPE: DNA
<213> ORGANISM: Artificial Sequence
<220> FEATURE:
<223> OTHER INFORMATION: reverse primer

<400> SEQUENCE: 18
ataatgtttt tatattatac atgttctaaa agaataatcg atacagttta ctagtataaa    60
aaggcgcgcc                                                           70

<210> SEQ ID NO 19
<211> LENGTH: 80
<212> TYPE: DNA
<213> ORGANISM: Artificial Sequence
<220> FEATURE:
<223> OTHER INFORMATION: forward primer

<400> SEQUENCE: 19
gttcgcggct aatcgcgata atgtagcttc tagacttttg tcctaatttt tataaaaatt    60
gaaaataaat acaaaggttc                                                80

<210> SEQ ID NO 20
<211> LENGTH: 77
<212> TYPE: DNA
<213> ORGANISM: Artificial Sequence
<220> FEATURE:
<223> OTHER INFORMATION: reverse primer

<400> SEQUENCE: 20
ctggacgaca cggatttatt aatatcgaaa aggatataat tgtatttag tttttatcta     60 gtataaaaag gcgcgcc                                                   77

<210> SEQ ID NO 21
<211> LENGTH: 77
<212> TYPE: DNA
<213> ORGANISM: Artificial Sequence
<220> FEATURE:
<223> OTHER INFORMATION: forward primer

<400> SEQUENCE: 21
atctaatgga taaactgaat ctaacaaaga gcgacgtaca actgttgtaa tttttatcta    60
gtataaaaag gcgcgcc                                                   77

<210> SEQ ID NO 22
<211> LENGTH: 80
<212> TYPE: DNA
```

```
<213> ORGANISM: Artificial Sequence
<220> FEATURE:
<223> OTHER INFORMATION: reverse primer

<400> SEQUENCE: 22
ctttgaaaga atgtttggtt caaaacctac attttacgaa gcataatttt tataaaaatt     60
gaaaataaat acaaaggttc                                                 80

<210> SEQ ID NO 23
<211> LENGTH: 95
<212> TYPE: DNA
<213> ORGANISM: Artificial Sequence
<220> FEATURE:
<223> OTHER INFORMATION: forward primer

<400> SEQUENCE: 23
gttgttggcg ttggtggcgc tagtcatcac attaactatt ttttattact ttatactata     60
atttttataa aaattgaaaa taaatacaaa ggttc                                95

<210> SEQ ID NO 24
<211> LENGTH: 80
<212> TYPE: DNA
<213> ORGANISM: Artificial Sequence
<220> FEATURE:
<223> OTHER INFORMATION: reverse primer

<400> SEQUENCE: 24
ttatggcagg tgagatgttt gttagaagtc agtctagtac tattatagta taattttat      60 ctagtataaa aaggcgcgcc                                                 80

<210> SEQ ID NO 25
<211> LENGTH: 80
<212> TYPE: DNA
<213> ORGANISM: Artificial Sequence
<220> FEATURE:
<223> OTHER INFORMATION: forward primer

<400> SEQUENCE: 25
ataagatatc ttctcaaaag atcaaggaaa tggaagaaac agaagacttt taatttttat     60
ctagtataaa aaggcgcgcc                                                 80

<210> SEQ ID NO 26
<211> LENGTH: 80
<212> TYPE: DNA
<213> ORGANISM: Artificial Sequence
<220> FEATURE:
<223> OTHER INFORMATION: reverse primer

<400> SEQUENCE: 26
gtttaaaaga cagatcatag aaaaatatgt tattgataag aattaatttt tataaaaatt     60
gaaaataaat acaaaggttc                                                 80

<210> SEQ ID NO 27
<211> LENGTH: 77
<212> TYPE: DNA
<213> ORGANISM: Artificial Sequence
<220> FEATURE:
<223> OTHER INFORMATION: forward primer

<400> SEQUENCE: 27
gttattttat gtcaccgcat tggtgttccg attttagtaa tatggaatag ttttatcta      60 gtataaaaag gcgcgcc                                                    77
```

<210> SEQ ID NO 28
<211> LENGTH: 80
<212> TYPE: DNA
<213> ORGANISM: Artificial Sequence
<220> FEATURE:
<223> OTHER INFORMATION: reverse primer

<400> SEQUENCE: 28
gctgttatgg ttccttacag gaacattcgt taccgcattt atctaatttt tataaaaatt      60
gaaaataaat acaaaggttc                                                  80

<210> SEQ ID NO 29
<211> LENGTH: 80
<212> TYPE: DNA
<213> ORGANISM: Artificial Sequence
<220> FEATURE:
<223> OTHER INFORMATION: forward primer

<400> SEQUENCE: 29
aggatgttat tacgaatcat taaaaaaatt aactgaggat gattgatttt tataaaaatt      60
gaaaataaat acaaaggttc                                                  80

<210> SEQ ID NO 30
<211> LENGTH: 77
<212> TYPE: DNA
<213> ORGANISM: Artificial Sequence
<220> FEATURE:
<223> OTHER INFORMATION: reverse primer

<400> SEQUENCE: 30
acaatcccgt tataaaaata cacgatggta aattaattta tattttctaa ttttatctag      60
gtataaaaag gcgcgcc                                                     77

<210> SEQ ID NO 31
<211> LENGTH: 77
<212> TYPE: DNA
<213> ORGANISM: Artificial Sequence
<220> FEATURE:
<223> OTHER INFORMATION: forward primer

<400> SEQUENCE: 31
tccatctaga ctatattatc aaaatttgga aacttcaaaa acgatattag ttttatctag      60
gtataaaaag gcgcgcc                                                     77

<210> SEQ ID NO 32
<211> LENGTH: 80
<212> TYPE: DNA
<213> ORGANISM: Artificial Sequence
<220> FEATURE:
<223> OTHER INFORMATION: reverse primer

<400> SEQUENCE: 32
agacttgatt gtgacattta gagaacgata ttcgtataaa ttctaatttt tataaaaatt      60
gaaaataaat acaaaggttc                                                  80

<210> SEQ ID NO 33
<211> LENGTH: 80
<212> TYPE: DNA
<213> ORGANISM: Artificial Sequence
<220> FEATURE:
<223> OTHER INFORMATION: forward primer

<400> SEQUENCE: 33
attgtttata ctcaagatat tcgttaaacg aattaaaatt atttaatttt tataaaaatt    60
gaaaataaat acaaaggttc                                                80

<210> SEQ ID NO 34
<211> LENGTH: 77
<212> TYPE: DNA
<213> ORGANISM: Artificial Sequence
<220> FEATURE:
<223> OTHER INFORMATION: reverse primer

<400> SEQUENCE: 34
aggaacagat taatccagac gattgttgtc tggatatggg aatgtattaa ttttatcta    60 gtataaaaag gcgcgcc                                                   77

<210> SEQ ID NO 35
<211> LENGTH: 77
<212> TYPE: DNA
<213> ORGANISM: Artificial Sequence
<220> FEATURE:
<223> OTHER INFORMATION: forward primer

<400> SEQUENCE: 35
gttacctccg cagtttttac gagcgatttc acgttcagcc ttcatgcgtc ttttatcta    60 gtataaaaag gcgcgcc                                                   77

<210> SEQ ID NO 36
<211> LENGTH: 80
<212> TYPE: DNA
<213> ORGANISM: Artificial Sequence
<220> FEATURE:
<223> OTHER INFORMATION: reverse primer

<400> SEQUENCE: 36
gtgacagaag ctaaacccga taacgataag cgaattcatg ctataatttt tataaaaatt    60
gaaaataaat acaaaggttc                                                80

<210> SEQ ID NO 37
<211> LENGTH: 80
<212> TYPE: DNA
<213> ORGANISM: Artificial Sequence
<220> FEATURE:
<223> OTHER INFORMATION: forward primer

<400> SEQUENCE: 37
attgataata taaatatgag cattagtatt tctgtggatt aatagatttt tataaaaatt    60
gaaaataaat acaaaggttc                                                80

<210> SEQ ID NO 38
<211> LENGTH: 77
<212> TYPE: DNA
<213> ORGANISM: Artificial Sequence
<220> FEATURE:
<223> OTHER INFORMATION: reverse primer

<400> SEQUENCE: 38
ttatgaggta tttagagatt agagatgatt aatgatcccc atactagaaa ttttatcta    60 gtataaaaag gcgcgcc                                                   77

EXPRESSION SYSTEM FOR EXPRESSING HERPESVIRUS GLYCOPROTEIN COMPLEXES

PRIORITY CLAIM

This application is a continuation of U.S. application Ser. No. 16/630,624, filed Jan. 13, 2020, which is a U.S. National Phase Application of International Application No. PCT/US2018/042046, filed Jul. 13, 2018, which claims priority to U.S. Provisional Application No. 62/532,298, filed Jul. 13, 2017, all of which are incorporated by reference herein in their entirety, including drawings.

STATEMENT OF GOVERNMENT INTEREST

This invention was made with government support under AI103960 awarded by the National Institutes of Health. The government has certain rights in the invention.

SEQUENCE LISTING

This application contains a Sequence Listing, which was submitted in ASCII format via EFS-Web, and is hereby incorporated by reference in its entirety. The ASCII copy, created on Jun. 8, 2022, is named SequenceListing.txt and is 11 KB in size.

BACKGROUND

Induction of neutralizing antibodies (NAbs) that block herpesvirus glycoprotein complex-mediated entry into host cells is considered important for a vaccine candidate to prevent or control herpesvirus infection. However, using herpesvirus glycoprotein complexes as antigens is complicated by the necessity of expressing multiple subunits simultaneously to allow efficient complex assembly and formation of conformational neutralizing epitopes.

Although protective immune correlates of human cytomegalovirus (HCMV) are only poorly defined, induction of humoral and cellular immune responses targeting immunodominant antigens such as the HCMV pentamer complex (PC), glycoprotein gB, or phosphoprotein pp65 is thought to be important for a vaccine candidate to prevent congenital HCMV infection. How these antigens can be assembled into a subunit vaccine to efficiently stimulate anti-HCMV immunity remains unknown.

There remains a need to inducing NAbs that effectively block herpesvirus infections using the corresponding assembled herpesvirus glycoprotein complexes as antigens. The technology disclosed herein satisfies this need.

SUMMARY

In one aspect, this disclosure relates to an expression system for expressing a herpesvirus glycoprotein complex. The expression system may include a vector inserted with two or more nucleic acid sequences that encode two or more subunits of the herpesvirus glycoprotein complex, linked by one or more linking sequences, such that the two or more subunits can be co-expressed simultaneously, self-cleaved and self-processed to assemble into the herpesvirus glycoprotein complex. The vector can be a plasmid vector or a viral vector. In some embodiments, the linking sequences include IRES and nucleic acid sequences encoding 2A peptides that mediate ribosomal skipping. In some embodiments, the vector is inserted with a single promoter before the two or more nucleic acid sequences such that the single promoter controls the expression of the two or more nucleic acid sequences.

In another aspect, a vaccine composition for preventing herpesvirus infection is provided. The vaccine composition may include a vector capable of co-expressing two or more subunits of a herpesvirus glycoprotein complex simultaneously and a pharmaceutically acceptable carrier, adjuvant, additive or combination thereof. In some embodiments, the two or more subunits are linked by one or more linking sequences, such that the two or more subunits can be co-expressed simultaneously, self-cleaved and self-processed to assemble into the herpesvirus glycoprotein complex. In some embodiments, the linking sequences include IRES and nucleic acid sequences encoding 2A peptides. In some embodiments, the vector is inserted with a single promoter before the two or more nucleic acid sequences such that the single promoter controls the expression of the two or more nucleic acid sequences.

In another embodiment, a method of preventing herpesvirus entry into a cell is provided. Such a method may include infecting the cell with an effective amount of a viral vector, the viral vector comprising two or more nucleic acids encoding two or more subunits of a herpesvirus glycoprotein complex, linked by one or more linking sequences.

In another embodiment, a method for preventing or treating a herpesvirus infection in a subject is provided. Such a method may include administering a therapeutically effective amount of a herpesvirus vaccine to the subject, wherein the herpesvirus vaccine comprises a vector capable of co-expressing two or more subunits of a herpesvirus glycoprotein simultaneously, and a pharmaceutically acceptable carrier, adjuvant, additive (e.g. CD40L) or combination thereof.

According to some of the embodiments described above, the viral vector is a modified vaccinia Ankara (MVA) and the glycoprotein complex is HCMV pentamer complex (PC) composed of its five subunits or antigenic fragments thereof: UL128, UL130, UL131A, glycoprotein L (gL), and glycoprotein H (gH). In some embodiments, the viral vector is further inserted with one or more additional DNA sequences that encode one or more additional HCMV proteins or antigenic fragments thereof. These additional proteins could be either the dominant targets of cell-mediated immunity such as pp65 and immediate early 1 and 2 proteins or other important humoral immune targets such as glycoproteins gB, gM, gN, or gO or antigenic fragments thereof.

BRIEF DESCRIPTION OF THE DRAWINGS

FIG. 1A shows MVA-BAC$^{TK}$ construction. pBeloBAC11 vector sequences (B=cat, OriS, repE, sopA/B/C, cos, loxP site) and a GFP expression cassette (GFP, Vaccinia P11 promoter) were inserted into the Thymidine kinase (TK) gene of the MVA genome utilizing ~700 bp homologous sequences (gray filled elements). 85 and 87=MVA ORFs 85 and (Accession Nr. U94848). FIG. 1B shows BAC restriction analysis. Purified MVA-BAC$^{TK}$ DNA was digested with the indicated enzymes, electrophoretically separated in a 0.7% agarose gel containing ethidium bromide, and imaged by UV light exposure. Obtained in vitro BAC restriction pattern were compared to in silico restriction pattern of MVA-BAC$^{TK}$. FIG. 1C shows gene insertion. An mRFP marker was inserted into MVA-BAC$^{TK}$ into the indicated MVA deletion sites (Del2, Del3, Del6) or intergenic regions between the given MVA ORFs of MVA (U94848). Panel D exemplifies expression of the mRFP marker after virus reconstitution. FIG. 10 shows gene expression. Viral foci of MVA-BAC$^{TK}$-derived virus with mRFP marker inserted into the MVA Del2 site (panel C) were imaged by fluorescence microscopy to verify expression of the mRFP marker within Del2 and the GFP marker of the BAC vector within the TK gene (panel A). FIG. 1E shows multi-step growth kinetics of MVA-BAC$^{TK}$ virus. BHK cells were infected in duplicates (6 well plates) with 0.05 MOI of MVA-BAC$^{TK}$-derived virus (MVA$^{TK}$) or wild-type MVA (MVA 1974/NIH clone 1), and virus titers (PFU/ml) were determined at the indicated time points.

FIGS. 2A and 2B show construction of MVA expressing P2A-linked HCMV PC subunits. FIG. 2A shows HCMV PC subunits (gH, gL, UL128, UL130, UL131A) linked by different P2A sequences (P2A1-P2A4) were inserted either all together into the MVA intergenic region 69/70 (IGR69/70) of MVA-BAC$^{TK}$ or MVA-BAC$^{Del3}$ to generate polycistronic vectors MVA$^{TK}$-PC2A1 and MVA$^{Del3}$-PC2A1, respectively, or separately as UL128/130/131A and gH/gL subunit subsets into the MVA deletion 2 (Del2) site and IGR69/70 of MVA-BAC$^{TK}$ to generate polycistronic vector MVA$^{TK}$-PC2A2. B=BAC vector; mH5=Vaccinia modified H5 promoter; Del3=MVA Deletion 3 site, TK=Thymidine kinase gene. FIG. 2B shows that P2A sequences (P2A1-P2A4) with different codon usage were used to link the HCMV PC subunits within the MVA constructs as indicated in A. Lower 4 lines indicate DNA sequences with mutated nucleotides (marked in colors) that were used to encode for the P2A peptide between the HCMV subunits (SEQ ID NOS: 2-5). Upper line shows the amino acid sequences of the P2A peptide (SEQ ID NO: 1).

FIG. 5A shows NAb titers (geometric mean titer) measured over a 24 weeks period. Balb/c mice (N=4 to 6) were prime/boost vaccinated in three weeks interval (black rectangles) with polycistronic MVA vector MVA$^{TK}$-PC2A1, MVA$^{Del3}$-PC2A1, or MVA$^{TK}$-PC2A2 (FIG. 2), or control vector MVA$^{Del3}$-PC. At week 0 (pre-immune serum), 3, 7, 13, and 24, HCMV specific NAb titer (log 10 NT50) in mouse sera were measured against HCMV strain TB40/E on ARPE-19 EC (continuous lines) or on MRC-5 FB (dashed lines). The dotted line indicates the limit of NAb detection. Bars represent 95% confidence intervals. FIG. 5B shows statistical analysis of NAb titers. Wilcoxon matched-pairs test was used to investigate differences of ARPE-19 EC and MRC-5 FB specific NAb titers at week 7 and week 24 in vaccine groups immunized with the indicated MVA vectors. P values less than 0.05 were indicated with *.

DETAILED DESCRIPTION

Figure 1A:
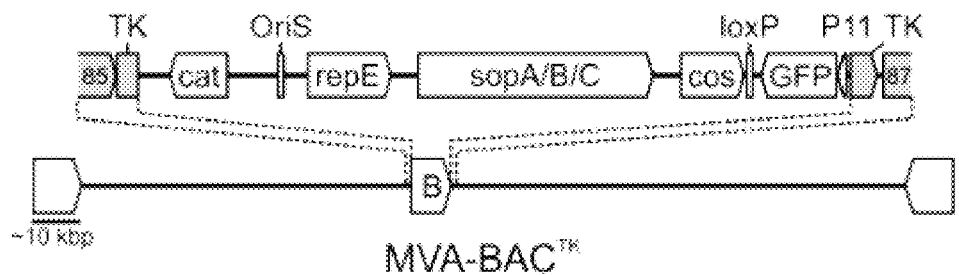
FIGS. 1A-1E show construction and characterization of MVA-BAC$^{TK}$.

Expression systems, vectors, vaccines for use in preventing or treating human herpesvirus infections are provided herein. The expression systems, vectors and vaccines, which are described in detail below, generate neutralizing antibodies (NAb) against human herpesvirus antigenic proteins or fragments to block entry of the human herpesvirus glycoprotein complex-mediated entry into host cells, thereby preventing horizontal and vertical virus transmission. This disclosure relates to the simultaneous expression of two or more herpesvirus glycoprotein complex subunits utilizing a linking sequence between the subunits to co-express self-processing polyproteins that efficiently assemble into protein complexes. The expressed subunits can encode for glycoproteins of any of the known human herpesvirus, including cytomegalovirus (CMV), varicella-zoster virus (VZV), Epstein-Barr virus (EBV), Kaposi's Sarcoma-associated herpesvirus (KSHV), herpes simplex virus type 1 (HSV-1), herpes simplex virus type 2 (HSV-2), human herpesvirus 6 (HHV-6), human herpesvirus 7 (HHV-7), or any other herpesvirus that infects vertebrates or invertebrates.

In some embodiments disclosed herein, the glycoprotein complex subunits can be either expressed by plasmid vectors such as pcDNA, pTT5, pCAGGS or related vectors, or viral vectors such as CMV, Vaccinia, Modified Vaccinia Ankara (MVA), Adenovirus, Sindbis virus, or related RNA or DNA-based viral vectors. The individual subunits can be linked by cleavage sequences such that the co-expressed subunits can be self-cleaved and self-assembled into glycoprotein complexes.

In some embodiments, the expression systems, vectors, vaccines described herein include one or more expression cassettes, each of which includes a single promoter and a sequence that encodes two or more herpesvirus glycoprotein complex subunits. As a result, the two or more herpesvirus glycoprotein complex subunits are co-expressed simultaneously, i.e., under control of a single promoter, obviating the need for multiple promoters or vectors. In certain embodiments, each expression cassette includes two, three, four, five, or even higher numbers of herpesvirus glycoprotein complex subunits, the expression of which are under control of a single promoter. In other embodiments, each expression cassette includes more than ten herpesvirus glycoprotein complex subunits. In some embodiments, a vector may include more than one such expression cassette.

In some embodiments, internal ribosome entry sites (IRES) can be introduced in between nucleic acid sequences encoding two or more herpesvirus glycoprotein complex subunits that are co-expressed, flanking the sequences encoding the two or more subunits. Although IRES can be used to link the expression of multiple genes under a single promoter, the use of multiple IRES sequences might be limited by size constraints or instability due to its relatively larger size comparing to 2A signal sequences. In some embodiments, 2A signal sequences that encode for the 2A peptide of food-and-mouth disease virus (F2A), equine rhinitis A virus (E2A), porcine teschovirus-1 (P2A), Thoseaasigna virus (T2A), cytoplasmic polyhedrosis virus (BmCPV 2A), or flacherie virus (BmIFV 2A) can be used to link multiple genes under a single promoter. 2A signal sequences have been found in picornaviruses, insect viruses and type C rotaviruses. Various suitable eukaryotic cell promoters can be used, including but not limited to, immediate-early I promoter of human CMV or the chicken beta actin promoter, promoters of vaccinia virus (mH5, pSyn, P11, p7.5), etc.

Additionally, a furin cleavage site preceding the 2A signal sequences can be incorporated to remove the 2A peptides following self-processing of the 2A-linked polyproteins. Furin is an enzyme that occurs in the Golgi apparatus and cleaves at very short signal peptides such as KKKR or RKKR motif. Furin cleavage contributes to protein processing and maturation. These short signal peptides can be added to the N-terminus of the 18-22 amino acid long 2A skipping signals so that they are removed following 2A-mediated processing of the herpesvirus glycoproteins, except for one or two remaining amino acids. The resultant product can be even more "native." Although it is preferred that the 2A-linked subunits are expressed all from one vector through the use of one or more expression cassettes, it is also possible to express the 2A-linked subunits from two or more separate vectors. As an example for this system, the P2A skipping system and a novel bacterial artificial chromosome (BAC) clone of the clinically deployable MVA vector were used to induce CMV NAb by self-processing subunits of the CMV pentamer complex. In some embodiments, using markerless BAC manipulation, codon-optimized and P2A-linked PC subunits can be inserted into MVA either into one insertion site to generate MVA-PC2A1, or as UL128/130/131A and gH/gL subunit subsets into two separate insertion sites to generate MVA-PC2A2. As detailed in the working examples, while all PC subunits were expressed in significantly higher levels from MVA-PC2A2 compared to MVA-PC2A1, the PC subunits of both polycistronic vectors were efficiently cleaved and transported to the cell surface as protein complexes forming conformational and linear neutralizing epitopes. In addition, vaccination of mice with two doses of either of the vaccine vectors resulted in potent and comparable HCMV specific NAb responses that remained stable for at least six months.

Despite the current Zika virus (ZIKV) outbreak in the Americas and its association with a surge of microcephaly, human cytomegalovirus (HCMV) remains the most common infectious cause of permanent birth defects worldwide (5, 31). While there are currently no vaccines that could protect pregnant women and their developing fetuses from either HCMV or ZIKV infection, vaccine development for HCMV unlike that for ZIKV spans almost a period of more than five decades (31, 36, 38). Many HCMV vaccine candidates have been preclinically and clinically evaluated, though encouraging findings for feasibility of a congenital HCMV vaccine have been obtained only with an approach based on envelope glycoprotein gB, a central mediator in HCMV host cell entry and important humoral immune target (30). In phase II clinical trials, gB adjuvanted with MF59 has been shown to afford 43 to 50% efficacy to prevent primary infection of HCMV seronegative (HCMV⁻) young women or adolescent girls (3, 37). While these efficacy rates are considered insufficient for vaccine licensure, these findings hold promise that a vaccine candidate with improved immunogenicity to elicit humoral and cellular immune responses could provide levels of protection that significantly alter the outcome of congenital HCMV infection.

Although it remains unclear why previous vaccine candidates have failed to effectively prevent HCMV infection, one explanation for their failure could be their inability to elicit certain types of neutralizing antibodies (NAb) (11). Over the last years it has been recognized that HCMV host cell infection occurs by two virus entry routes that are blocked by NAb of varying specificity and potency (29, 40). While HCMV infection of all susceptible cell types appears to depend on envelope glycoproteins gB and gH/gL/gO, the pentamer complex (PC) composed of gH, gL, UL128, UL130, and UL131A is additionally required for virus entry into many biologically relevant host cells including epithelial cells (EC), but dispensable for virus entry into other important cells such as fibroblasts (FB) (1, 20, 22, 50, 51, 55, 59, 64). Important for vaccine design, NAb predominantly recognizing quaternary conformational epitopes of the PC are substantially more potent than NAb interfering with gB and gH/gL/gO entry function (7, 17, 29). Since HCMV NAb were almost exclusively correlated with measurements based on FB before the identification of anti-PC antibodies, previous vaccine strategies such as those employing only gB were not designed to account for the potent NAb responses blocking EC entry (11, 18). Overall these findings suggest that inclusion of the PC into a vaccine candidate could eliminate a caveat of previous HCMV vaccines in eliciting NAb and, hence, lead to protection efficacy higher than that achievable with gB alone.

While there are only a few findings that support an important protective role of NAb targeting the PC (26, 27), many preclinical vaccine concepts based on the PC have been developed to stimulate HCMV NAb responses (16, 23, 58, 60, 62). These vaccine approaches consistently demonstrate that the PC is superior to gB and gH/gL in inducing NAb that prevent EC infection. A recently developed PC-specific vaccine concept was based on the well-characterized and clinically well-tolerated Modified Vaccinia Ankara (MVA) vector (7, 60, 62). In addition to its excellent safety record (19, 52), MVA provides many advantages over other vector systems including a large capacity for heterologous antigens, ability to elicit robust antigen specific immunity, and a versatile cytoplasmic expression system that allows efficient antigen delivery without the risk for viral DNA integration into host chromosomes (6, 9, 15). By utilizing MVA bacterial artificial chromosome (BAC) technology, multiple MVA insertion sites can be used to generate a single MVA vector co-expressing all five HCMV PC subunits (60). For example, the heterologous sequences can be inserted into TK site, one of the six major deletion sites (Del1-6), or MVA intergenic regions (there are over 180 MVA genes), or non-essential genes to drive gene expression by intrinsic promoter elements. This vector, termed MVA-PC, stimulated potent and durable HCMV specific NAb responses in mice and rhesus macaques (RM). However, while effective in eliciting NAb, MVA-PC appeared limited in accommodating additional HCMV antigens to further enhance its ability to induce anti-HCMV immune responses due to the complexity of the vector design to co-express all five HCMV PC subunits (60).

By exploiting the ribosomal skipping mechanism conferred by 2A peptides (14, 39), an approach of expressing the five HCMV PC subunits from MVA as only one or two self-processing polyproteins is disclosed herein. The 2A ribosomal skipping system is widely-used to express multi-protein complexes due to the relative small sizes of 2A peptides (18-22 amino acids) and because it allows stoichiometric expression of the individual 2A-linked subunits (12, 24, 45). As demonstrated in the working examples, by utilizing a novel BAC of MVA, codon-optimized and P2A-linked DNA sequences of the five PC subunits were inserted into MVA either all together into only one insertion site or as UL128/130/131A and gH/gL subunit subsets into two separate insertion sites, resulting in MVA-PC2A1 and MVA-PC2A2, respectively. Whereas expression levels of all five PC subunits were significantly higher with MVA-PC2A2 than with MVA-PC2A1, the PC subunits expressed from both vaccines were efficiently cleaved and transported to the cell surface as five member protein complexes that formed conformational neutralizing epitopes. In addition, vaccination of mice with two doses of either MVA-PC2A1 or MVA-PC2A2 resulted in induction of potent and durable HCMV NAb responses. This approach of eliciting NAb by self-processing PC polyproteins significantly reduces the complexity of simultaneously co-expressing all five PC subunits, which could be useful for many other vector systems to efficiently express the PC and stimulate HCMV specific NAb and may serve as a template to induce NAb by multi-protein glycoprotein complexes of other viruses.

Since the discovery of the HCMV PC and its recognition as a target of potent NAb responses that prevent in vitro HCMV infection of many biologically-relevant host cells (7, 29, 55), the HCMV PC has become a major focus in HCMV vaccine development (16, 23, 58, 60, 62). As most of these potent NAb recognize quaternary conformational epitopes formed by more than one subunit of the PC (7, 29), vaccine-mediated NAb induction based on the PC relies on simultaneous co-expression of all five PC subunits to enable efficient subunits assembly and formation of conformational neutralizing epitopes. While the large insertion capacity and versatile expression system of MVA are advantageous (60, 62), others have mastered it by employing replication defective HCMV (16) or viral vector or plasmid expression constructs with multiple promoter elements or internal ribosomal entry sites (IRES) (21, 28, 58). In addition, Kabanova and colleagues developed a vaccine approach based on purified PC protein that was generated via 2A-linked expression constructs; however details of the vector construction to produce the purified PC protein remained unclear (23).

Disclosed herein is an expression system based on ribosomal skipping mechanism, i.e., by P2A peptides of porcine teschovirus-1 to induce HCMV NAb by MVA vectors expressing self-processing PC subunits inserted into only one or two MVA insertion sites (FIG. 2). Because of the relatively small sequence of the P2A peptides and the use of identical 2A peptides for polyprotein cleavage (FIG. 2) (24, 45), this system can be used for other vector systems to efficiently express the PC and to stimulate HCMV NAb and may form a template for stimulating NAb by multi-subunit glycoprotein complexes of other viruses as well. Although PC and inducing HCMV NAb are used as examples in this disclosure, expression and assembly of other herpesvirus glycoprotein complexes can be achieved based on this disclosure.

Besides introducing an approach for stimulating potent NAb by self-cleavable PC subunits, also disclosed herein is a novel BAC clone of MVA that can serve as a powerful tool to develop clinically deployable vaccine vectors for infectious diseases and cancer (FIG. 1). While the conventional way of producing recombinant MVA by homologous recombination in eukaryotic cells may be as efficient as the BAC technology to generate antigenically less complex MVA vectors, the BAC technology appears to be in particular useful to generate MVA with multiple antigen insertions due to the possibility of repeatedly and seamlessly manipulate BAC DNA by highly-efficient and versatile mutagenesis techniques (8, 10, 60). In contrast to two previously generated MVA-BAC—including original MVA-BAC$^{Del3}$-(8, 35), the construction of MVA-BAC$^{TK}$ was based on the insertion of BAC vector sequences into the TK gene locus. As demonstrated in the working examples, the BAC restriction and sequencing analysis as well as growth kinetics of BAC-derived virus suggest that MVA-BAC$^{TK}$ comprises an intact, full-length genomic clone of MVA. In addition, the comparable and potent HCMV specific NAb responses induced by the polycistronic MVA vectors derived from MVA-BAC$^{TK}$ and the immunologically well-characterized original MVA-BAC$^{Del3}$ indicate that MVA-BAC$^{TK}$ has excellent immunogenicity properties to stimulate antigen specific immunity. Accordingly, the MVA-BAC$^{TK}$ disclosed herein can be used for developing antigenically complex recombinant MVA vaccine vectors.

The MVA-BAC$^{TK}$-derived polycistronic MVA vectors expressing self-processing HCMV PC subunits disclosed herein can be used for developing a multi-component MVA vaccine candidate to prevent congenital HCMV infection. By linking the PC subunits together via P2A peptides allowing expression of all five PC subunits using only one or two MVA insertion sites, the complexity of the MVA vector construction is reduced significantly compared to MVA$^{Del3}$-PC to simulate potent HCMV NAb responses (60). As the developed MVA vectors expressing P2A-linked PC subunits are as potent as MVA$^{Del3}$-PC to stimulate HCMV NAb in mice, it can be anticipated that the polycistronic MVA vectors will also elicit NAb in non-human primates considering our previous finings with MVA$^{Del3}$-PC (60). As a consequence of reducing the insertion of the PC subunits to only one or two MVA insertion sites, other commonly used MVA insertion sites remain available for introducing additional HCMV antigens such as gB and pp65 to further enhance the ability of the developed polycistronic MVA vectors to stimulate anti-HCMV humoral and cellular immune responses. In addition, non-commonly used MVA insertion sites can be used for additional antigen insertion based on the demonstration of inserting mRFP into 12 different insertion sites distributed over the cloned MVA genome of MVA-BAC$^{TK}$ (FIG. 1).

Figure 3:
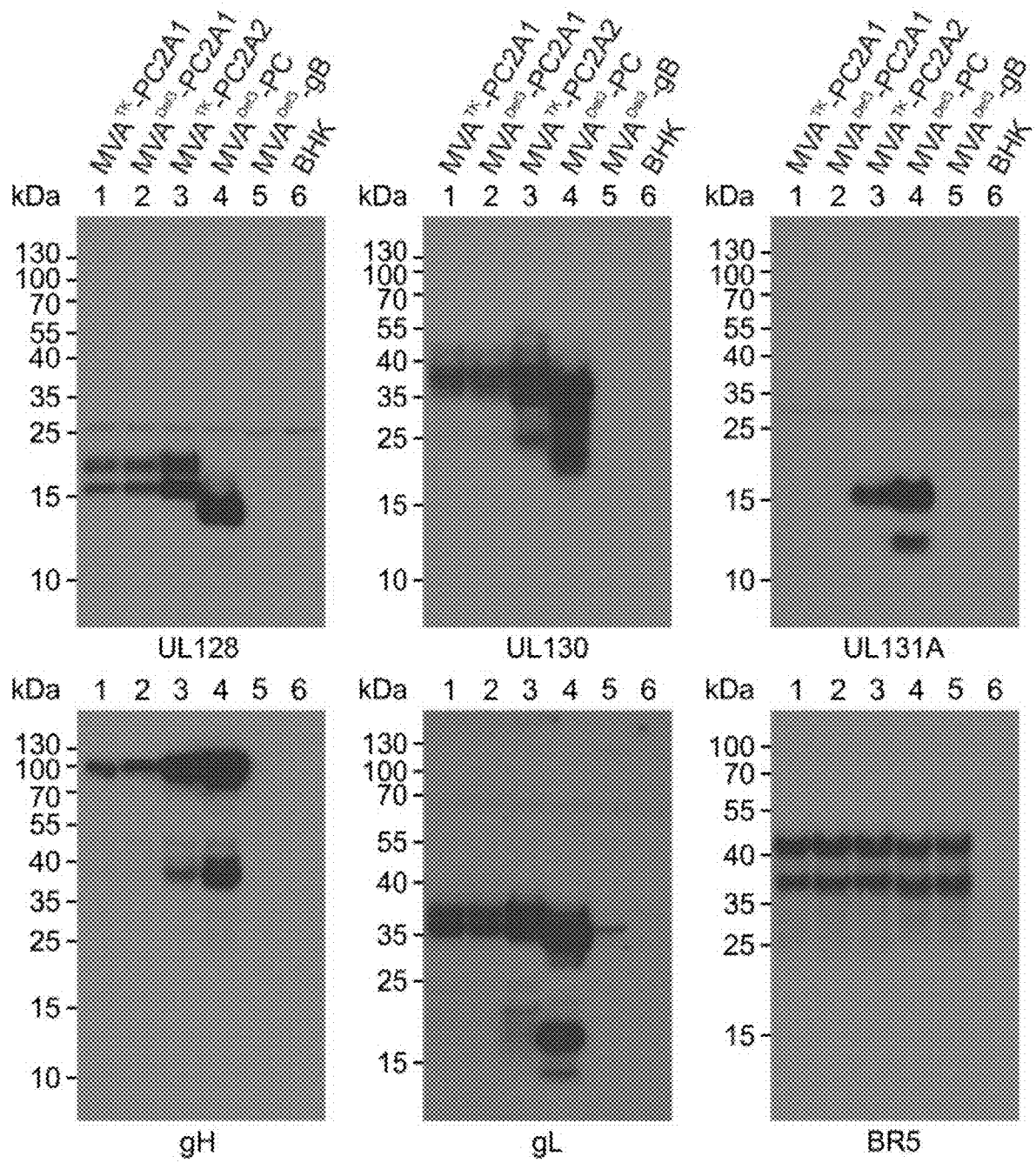
FIG. 3 shows expression and cleavage of P2A-linked PC subunits expressed from MVA vectors. BHK cells were infected with the polycistronic MVA vectors MVA$^{TK}$-PC2A1, MVA$^{Del3}$-PC2A1, and MVA$^{TK}$-PC2A2 (FIG. 2), control vectors MVA$^{Del3}$-PC or MVA$^{Del3}$-gB, or mock (BHK; uninfected), and HCMV PC subunits (gH, gL, UL128, UL130, UL131A) were detected in whole cell lysates by Immunoblot using MAb and polyclonal antisera specific for the individual HCMV PC subunits. Vaccinia protein BR5 was detected within the different samples as a loading control. kDa=kilo Dalton.
Figure 4:
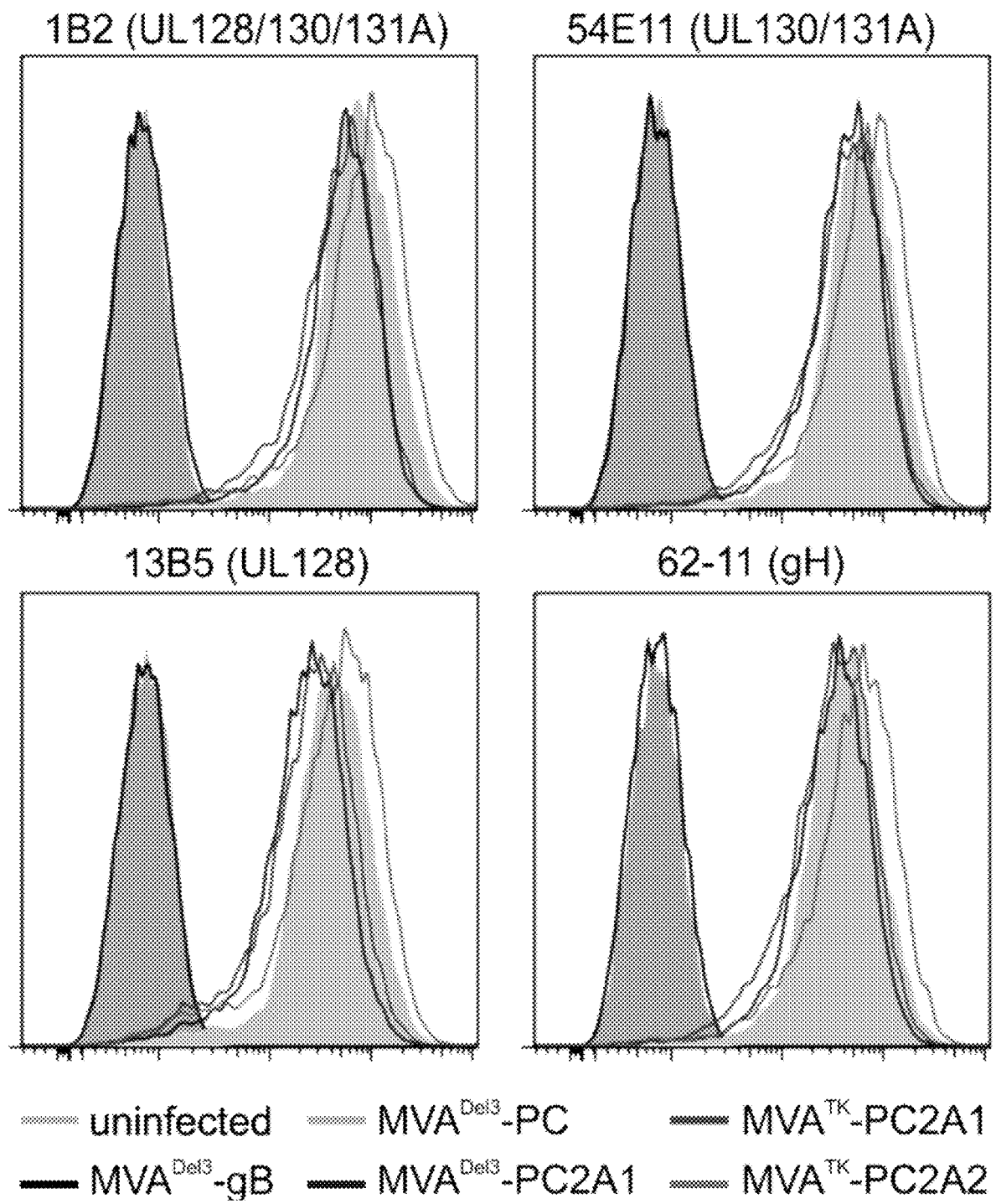
FIG. 4 shows cell surface detection of MVA expressed P2A-linked PC subunits by NAb. BHK cells were infected with polycistronic MVA vector MVA$^{TK}$-PC2A1, MVA$^{Del3}$-PC2A1, or MVA$^{TK}$-PC2A2 (FIG. 2), control vector MVA$^{Del3}$-PC or MVA$^{Del3}$-gB, or mock (BHK; uninfected). Live, non-permeabilized cells were investigated by cell surface Flow cytometry staining using NAb specific for quaternary conformational epitopes formed by HCMV PC subunits UL128/UL130/UL131A (1B2) or UL130/131A (54E11), or for epitopes constituted by UL128 (1365) or gH (62-11). Following addition of primary antibodies, cells were incubated with anti-mouse Alexa Fluor 647 secondary antibody. Histogram axes represent fluorescence intensity (X-axis) and cell count (Y-axis).

Despite expressing the PC subunits of the different MVA vectors by the same vaccinia promoter (mH5), MVA$^{TK}$-PC2A2 with PC subunit subsets inserted into two separate insertion sites expressed significantly lower amounts of the HCMV proteins compared to MVA$^{Del3}$-PC, and lowest PC subunit expression was observed with the pentacistronic vectors MVA$^{TK}$-PC2A1 and MVA$^{Del3}$-PC2A1 (FIG. 3). While it appeared that the pentacistronic vectors did not express detectable amounts of UL131A by Immunoblot, the cell surface Flow Cytometry staining analysis using antibodies to conformational epitopes constituted by UL128/130/131A and UL130/131A provide evidence that these vectors expressed also UL131A in addition to all other four PC subunits (FIG. 4). While the reason for the variable PC subunit expression levels between the MVA vectors remain unknown, they appear to be associated with the length of the inserted sequences, which may lead to different transcription or translation efficacy or differences in post transcriptional and translation processing of the PC subunits. Equally as likely, the co-translational P2A skipping mechanism may impair processing of the nascent self-processing PC polyproteins, and the higher the number of cleavage signals within the expression construct the less efficient the expression. However, the differences in PC subunit expression levels between the three polycistronic vectors and MVA$^{Del3}$-PC may also be a result of different codon-usage, since the self-processing PC subunits of the polycistronic MVA vectors were encoded by codon-optimized DNA sequences while the PC subunits of MVA$^{Del3}$-PC were encoded by DNA sequences identical to those present in HCMV TB40/E.

Figure 5A:
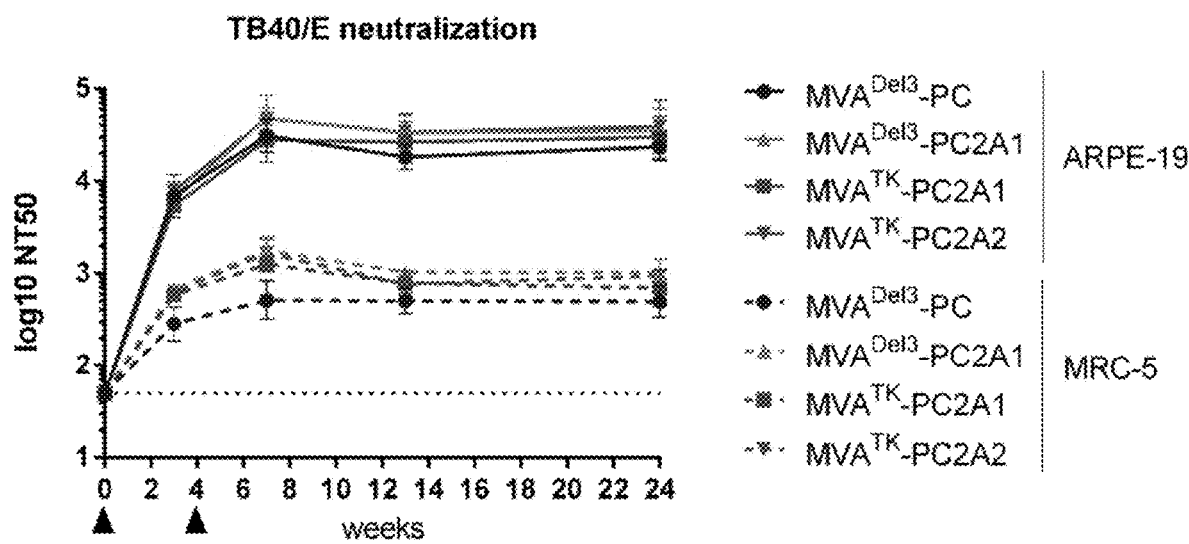
FIGS. 5A and 5B show NAb induction by MVA vectors expressing P2A-linked PC subunits.
Figure 5B:
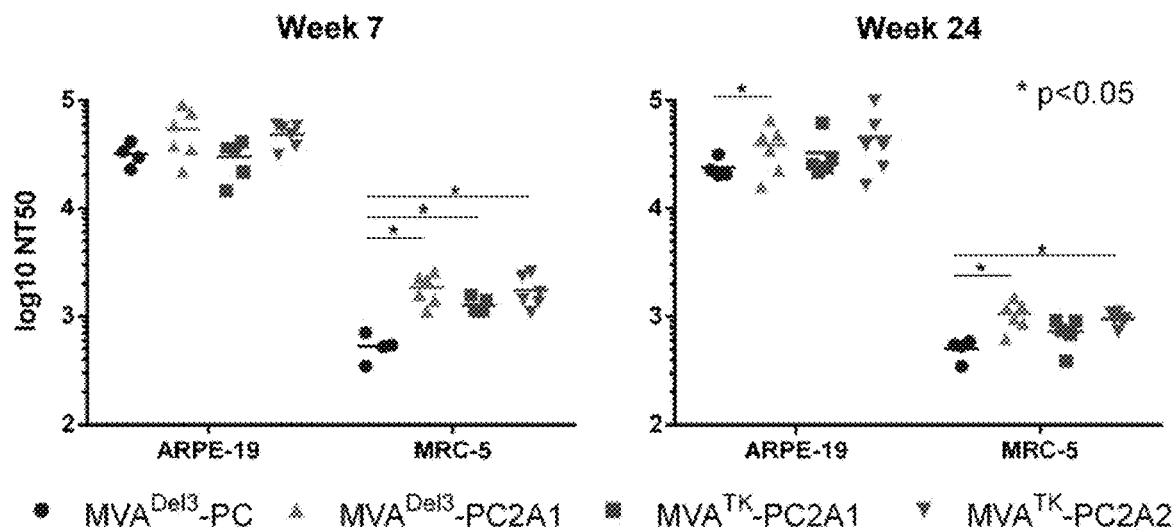

Considering the marked differences in PC subunit expression of the polycistronic MVA vectors and MVA$^{Del3}$PC, it was unexpected that these vectors stimulated comparable HCMV specific NAb responses (FIGS. 3 and 5). This discrepancy in PC subunit expression and PC-specific NAb induction could be explained by the observations made for cell surface detection of the PC subunits. While cellular PC subunit expression levels of the different vectors were significantly different by Immunoblot (FIG. 3), comparable cell surface Flow cytometry staining intensity of the PC subunits using different NAb was observed for all MVA vectors (FIG. 4), suggesting that the PC subunits expressed from the polycistronic MVA vectors and MVA$^{Del3}$PC were transported to the cell surface with similar efficacy. This could explain why the different vectors had similar ability to stimulate HCMV specific NAb, despite expressing different amounts of HCMV subunits. Consequently, only very low expression levels of the PC subunits appear to be required for stimulating anti-HCMV NAb responses, at least when considering NAb induction in mice. MVA$^{TK}$-PC2A2 and MVA$^{Del3}$-PC may therefore overexpress a proportion of the PC subunits, potentially resulting in inefficient processing or assembly of the PC subunits. In this context, comparing NAb induction by the different MVA vectors in mice by dose de-escalation may help to distinguish whether the MVA vectors have different ability to stimulate HCMV NAb. As all three polycistronic MVA vectors stimulated potent NAb responses in mice, they all represent a basis to develop a multi-component MVA vaccine vector for preventing congenital HCMV infection.

While there are many innovative vaccine candidates to mitigate congenital HCMV infection, of which one has recently entered phase I clinical testing (54), the approach for developing a congenital HCMV vaccine candidate disclosed herein is attractive for the following reasons. First, it is based on the highly-attenuated MVA vaccine vector that has been tested safely on over 120000 people in Europe (19, 52), indicating that the vaccine approach will be clinically deployable. Second, MVA is well-known to elicit robust antigen specific humoral and cellular immune responses (9, 15), suggesting that the approach would allow to effectively induce HCMV immune responses by multiple antigens. This is supported by the recently published phase I clinical results for an MVA vector expressing immunodominant T cell targets pp65 and 1E1/2 that induced potent and durable antigen specific cellular immune responses in healthy adults (25). Third, it is based on vaccine construction using BAC technology that will allow to effectively exploit the large insertion capacity and versatile expression system of MVA to assemble multiple HCMV antigens including the PC, gB, and pp65 into a single MVA vector (8, 60). Fourth, it is based on the expression of a membrane tethered PC that allows induction of potent HCMV specific NAb responses in mice and RM by only two immunizations (60). For these reasons, the vaccine approach disclosed herein may represent a unique strategy to develop a multi-component vaccine to mitigate congenial HCMV disease.

Based on the studies described above, expression systems, viral vectors and vaccines that may be used in methods for inhibiting of herpesvirus entry into host cells have been developed and described herein.

Expression Systems, Vectors and Vaccines

According to the embodiments described herein, a herpesvirus antigenic protein expression system (or "antigen expression system") is provided herein. In one embodiment, the antigen expression system may include a cloning vector to clone an expression vector that is able to express one or more herpesvirus antigenic proteins or antigenic fragments thereof. In some embodiments, the antigenic proteins or antigenic fragments thereof are herpesvirus glycoprotein complex, subunits thereof, or antigenic fragments of one or more subunits. The herpesvirus glycoprotein complex subunits or antigenic fragments thereof are derived from cytomegalovirus (CMV), varicella-zoster virus (VZV), Epstein-Barr virus (EBV), Kaposi's Sarcoma-associated herpesvirus (KSHV), herpes simplex virus type 1 (HSV-1), herpes simplex virus type 2 (HSV-2), human herpesvirus 6 (HHV-6), human herpesvirus 7 (HHV-7), or any other herpesvirus that infects vertebrates or invertebrates.

In one embodiment, the cloning vector is a BAC, which is a DNA construct that may be used to clone one or more target herpesvirus genes by transformation in bacteria (e.g., E. coli). The use of BAC as a cloning vector allows for stable cloning of very large DNA sequences, and can be easily manipulated using genetic techniques established for E. coli. In some embodiments, the BAC cloning vector is used to clone an expression vector. The expression vector may be a plasmid, a BAC, a viral vector (e.g., adenoviral vectors, adeno-associated viral vectors, RNA viral vectors, lentiviral vectors or retroviral vectors), a viral vector constructed as a BAC, or any other suitable vector that is able to express a recombinant protein, a viral vector or both.

In some embodiments, the expression vector (e.g., the viral vector) is capable of expressing one or more immunogenic or antigenic herpesvirus proteins or functional fragments thereof. An immunogenic protein is a protein that, when introduced to a subject, is recognized by the subject's immune cells, thereby stimulating an immune reaction. The immune reaction may result in antibody production (e.g., neutralizing antibody production) against that protein. A functional or antigenic fragment of an immunogenic protein is any portion of the protein that contains an antigenic portion of the protein or is an antigenic portion of the protein which may contain at least one epitope. In some embodiments, the one or more immunogenic proteins or functional fragments thereof may be an immunogenic protein complex, which includes a set of immunogenic protein subunits or functional fragments thereof.

In one embodiment, the BAC cloning vector is used to clone a viral expression vector. In such embodiments, the BAC vector is inserted into the genome of the viral expression vector to generate a virus-BAC construct or plasmid. A bacterial host (e.g., E. coli) is then transfected with the virus-BAC plasmid to clone the viral vector. Transfection of the virus-BAC clones into eukaryotic cells susceptible to infection by the viral vector results in reconstitution of the recombinant virus. The resulting reconstituted viral vectors may then be used to infect target tissues or cells in a host.

In some embodiments, the glycoprotein complex subunits can be expressed by plasmid vectors such as pcDNA, pTT5, pCAGGS or related vectors. In some embodiments, the expression vector can be a viral vector derived from any suitable adenovirus, sindbis virus, CMV, or poxvirus including, but not limited to, Avipoxvirus (e.g., canarypox virus and related strains such as ALVAC; fowlpox virus), Orthopoxvirus (e.g., vaccinia virus strains such as the Western Reserve or Lister strain, Copenhagen strain (NYVAC), Dryvax strain, modified vaccinia Ankara (MVA) strain, ACAM1000, and ACAM2000 strain), Parapoxvirus (e.g., Orf virus). In one embodiment, the viral vector is a modified vaccinia Ankara (MVA), which is cloned into the BAC cloning vector ("MVA-BAC") and is able to express one or more immunogenic herpesvirus proteins or antigenic fragments thereof. Any suitable MVA strain may be cloned by a BAC in accordance with the embodiments described herein, including, but not limited to the 1974-MVA strain, VR strain or ACAM 3000 strain.

In one embodiment, one or more immunogenic herpesvirus proteins or antigenic fragments thereof are HCMV glycoproteins including a set of immunogenic protein subunits or functional fragments thereof that are part of a CMV pentamer complex (PC). The CMV pentamer complex is a HCMV protein complex that includes the following five immunogenic protein subunits or functional fragments thereof: UL128, UL130, UL131A, gL, and gH. Co-expression of all five of the PC subunits is required in single cells to obtain functional expression. Therefore, a single delivery vector is needed, since there is no current generally acceptable approach to guide >1 individual DNA or viral vectors to assemble a protein complex in vivo by co-expression of all 5 PC components.

Simultaneous co-expression of the PC complex that includes the UL128, UL130, UL131A, gL, and gH proteins or antigenic fragments thereof by the expression systems and viral vectors described herein results in stimulation of neutralizing antibodies (NAb) by a host's immune system that block HCMV infection in susceptible cells such as epithelial and endothelial cells.

In other embodiments, the expression vector may include additional HCMV proteins including, but not limited to, pp65, gB, 1E1 gM, gN, gO, and other suitable antigenic HCMV proteins known in the art. These additional genes may be inserted into a first expression vector with the PC subunits, or alternatively, may be inserted into a second expression vector to be administered in combination with the first expression vector. In some embodiments, all subunits are inserted into the same insertion site of an MVA-BAC vector, such as the TK insertion site. In other embodiments, one or more subunits are inserted into two or more different insertion sites of an MVA-BAC vector.

According to the embodiments described herein, an immunization regimen is provided. The immunization regimen may include plasmids, viral vectors, live-attenuated viruses, purified protein, or virus-like particles that express or comprise the herpesvirus glycoprotein complex subunits. The immunization regimen may be administered via prime/boost homologous (e.g. using only the same vaccine type) or heterologous (e.g using different vaccine types) vaccination. The immunization regimen may be administered in a dose vaccination schedule involving two or more immunizations, which may be administered 2 weeks to 6 month apart.

In other embodiments, the MVA vector described above may be a priming immunization. In such a case, the aforementioned primes can also be used as booster vectors after one or more (e.g., one, two, three, four, or more) consecutive MVA immunizations. Alternatively, priming and boosting vectors can alternate such that the heterologous immunization will include an MVA or alternate vector as a prime followed by MVA or an alternate vector as a boost from 1 to 4 times as an example. Other suitable immunization schedules or regimens that are known in the art may be used according to the embodiments described herein by those skilled in the art.

According to some embodiments, the nucleic acid sequences encoding two or more subunits of a herpesvirus glycoprotein complex are assembled into a single vector, with a linking sequence inserted between the nucleic acid sequences encoding two or more subunits. For example, CMV pentamer complex subunits may be linked through linking sequences such as internal ribosome entry sites (IRES), derived from a number of different RNA viruses that are well known in the art and sequences encoding 2A peptides, to link all or a portion of the subunits in one insertion site or multiple insertion sites. The 2A signal sequence encoding a 2A peptide of foot-and-mouth disease virus (F2A), a 2A peptide of equine rhinitis A virus (E2A), a 2A peptide of porcine teschovirus-1 (P2A), a 2A peptide of cytoplasmic polyhedrosis virus (BmCPV 2A), a 2A peptide of flacherie virus (BmIFV 2A), or a 2A peptide of Thosea asigna virus (T2A), can be used.

A recombinant vector, such as the MVA viral vector described above; or any other suitable alternative vector including suitable primer or booster vectors described above, may be part of a herpesvirus vaccine composition that may be used in methods to treat or prevent herpesvirus infection. The vaccine composition as described herein may comprise a therapeutically effective amount of a recombinant viral vector as described herein, and further comprising a pharmaceutically acceptable carrier according to a standard method. Examples of acceptable carriers include physiologically acceptable solutions, such as sterile saline and sterile buffered saline.

In some embodiments, the vaccine or pharmaceutical composition may be used in combination with a pharmaceutically effective amount of an adjuvant to enhance the anti-CMV effects. Any immunologic adjuvant that may stimulate the immune system and increase the response to a vaccine, without having any specific antigenic effect itself may be used as the adjuvant. Many immunologic adjuvants mimic evolutionarily conserved molecules known as pathogen-associated molecular patterns (PAMPs) and are recognized by a set of immune receptors known as Toll-like Receptors (TLRs). Examples of adjuvants that may be used in accordance with the embodiments described herein include Freund's complete adjuvant, Freund's incomplete adjuvant, double stranded RNA (a TLR3 ligand), LPS, LPS analogs such as monophosphoryl lipid A (MPL) (a TLR4 ligand), flagellin (a TLR5 ligand), lipoproteins, lipopeptides, single stranded RNA, single stranded DNA, imidazoquinolin analogs (TLR7 and TLR8 ligands), CpG DNA (a TLR9 ligand), Ribi's adjuvant (monophosphoryl-lipid A/trehalose dicorynoycolate), glycolipids (α-GalCer analogs), unmethylated CpG islands, oil emulsion, liposomes, virosomes, saponins (active fractions of saponin such as QS21), muramyl dipeptide, alum, aluminum hydroxide, squalene, BCG, cytokines such as GM-CSF and IL-12, chemokines such as MIP 1-α and RANTES, activating cell surface ligands such as CD40L, N-acetylmuramine-L-alanyl-D-isoglutamine (MDP), and thymosin α1. The amount of adjuvant used can be suitably selected according to the degree of symptoms, such as softening of the skin, pain, erythema, fever, headache, and muscular pain, which might be expressed as part of the immune response in humans or animals after the administration of this type of vaccine.

In further embodiments, use of various other adjuvants, drugs or additives with the vaccine of the invention, as discussed above, may enhance the therapeutic effect achieved by the administration of the vaccine or pharmaceutical composition. The pharmaceutically acceptable carrier may contain a trace amount of additives, such as substances that enhance the isotonicity and chemical stability. Such additives should be non-toxic to a human or other mammalian subject in the dosage and concentration used, and examples thereof include buffers such as phosphoric acid, citric acid, succinic acid, acetic acid, and other organic acids, and salts thereof; antioxidants such as ascorbic acid; low molecular weight (e.g., less than about 10 residues) polypeptides (e.g., polyarginine and tripeptide) proteins (e.g., serum albumin, gelatin, and immunoglobulin); amino acids (e.g., glycine, glutamic acid, aspartic acid, and arginine); monosaccharides, disaccharides, and other carbohydrates (e.g., cellulose and derivatives thereof, glucose, mannose, and dextrin), chelating agents (e.g., EDTA); sugar alcohols (e.g., mannitol and sorbitol); counterions (e.g., sodium); nonionic surfactants (e.g., polysorbate and poloxamer); antibiotics; and PEG.

The vaccine or pharmaceutical composition containing a recombinant viral vector described herein may be stored as an aqueous solution or a lyophilized product in a unit or multiple dose container such as a sealed ampoule or a vial.

Preventing Herpesvirus Entry into a Cell, Treating and Preventing Herpesvirus Infection The antigen expression system described above may be used in in vitro, in vivo or ex vivo methods of preventing herpes virus entry into a cell or a population of cells. In some embodiments, methods for preventing herpesvirus entry into a cell or a population of cells include steps of infecting the cell or population of cells with an effective amount of a viral vector capable of expressing a herpesvirus glycoprotein complex or antigenic fragments thereof.

In other embodiments, methods for treating or preventing a herpesvirus infection in a subject are provided. Such methods may include administering a therapeutically effective amount of a herpesvirus vaccine to the subject. The herpesvirus vaccine may include at least one active ingredient, wherein the at least one active ingredient includes a viral vector that is capable of expressing a herpesvirus glycoprotein complex or antigenic fragments thereof, such as those described herein.

The expression systems, vectors and vaccines described herein may be used to treat or prevent any herpesvirus infection. For example, HCMV infection that infects epithelial cells, endothelial cells, fibroblasts or a combination thereof can be treated or prevented. Examples of HCMV infections that may be treated or prevented using the methods described herein may include, but is not limited to, congenital HCMV infection, opportunistic HCMV infections in subjects with compromised immune system (e.g., organ and bone marrow transplant recipients, cancer patients and chemotherapy recipients, patients receiving immunosuppressive drugs and HIV-infected patients) and silent HCMV infections in otherwise healthy subjects.

The term "effective amount" as used herein refers to an amount of a composition that produces a desired effect. For example, a population of cells may be infected with an effective amount of a viral vector to study its effect in vitro (e.g., cell culture) or to produce a desired therapeutic effect ex vivo or in vitro. An effective amount of a composition may be used to produce a therapeutic effect in a subject, such as preventing or treating a target condition, alleviating symptoms associated with the condition, or producing a desired physiological effect. In such a case, the effective amount of a composition is a "therapeutically effective amount," "therapeutically effective concentration" or "therapeutically effective dose." The precise effective amount or therapeutically effective amount is an amount of the composition that will yield the most effective results in terms of efficacy of treatment in a given subject or population of cells. This amount will vary depending upon a variety of factors, including but not limited to the characteristics of the composition (including activity, pharmacokinetics, pharmacodynamics, and bioavailability), the physiological condition of the subject (including age, sex, disease type and stage, general physical condition, responsiveness to a given dosage, and type of medication) or cells, the nature of the pharmaceutically acceptable carrier or carriers in the formulation, and the route of administration. Further an effective or therapeutically effective amount may vary depending on whether the composition is administered alone or in combination with another composition, drug, therapy or other therapeutic method or modality. One skilled in the clinical and pharmacological arts will be able to determine an effective amount or therapeutically effective amount through routine experimentation, namely by monitoring a cell's or subject's response to administration of a composition and adjusting the dosage accordingly. For additional guidance, see Remington: The Science and Practice of Pharmacy, 21st Edition, Univ. of Sciences in Philadelphia (USIP), Lippincott Williams & Wilkins, Philadelphia, Pa., 2005, which is hereby incorporated by reference as if fully set forth herein.

"Treating" or "treatment" of a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof. Treatment may also mean a prophylactic or preventative treatment of a condition.

In some embodiments, the vaccine or pharmaceutical composition described herein may be used in combination with other known pharmaceutical products, such as immune response-promoting peptides and antibacterial agents (synthetic antibacterial agents). The vaccine or pharmaceutical composition may further comprise other drugs and additives. Examples of drugs or additives that may be used in conjunction with a vaccine or pharmaceutical composition described herein include drugs that aid intracellular uptake of the recombinant virus or MVA or recombinant transgenic protein of the present invention, liposome and other drugs and/or additives that facilitate transfection, (e.g., fluorocarbon emulsifiers, cochleates, tubules, golden particles, biodegradable microspheres, and cationic polymers).

In some embodiments, the amount of the active ingredient contained in the vaccine or pharmaceutical composition described herein may be selected from a wide range of concentrations, Virus Particle Unit (VPU), Plaque Forming Unit (PFU), weight to volume percent (w/v %) or other quantitative measure of active ingredient amount, as long as it is a therapeutically or pharmaceutically effective amount. The dosage of the vaccine or pharmaceutical composition may be appropriately selected from a wide range according to the desired therapeutic effect, the administration method (administration route), the therapeutic period, the patient's age, gender, and other conditions, etc.

In some aspects, when a recombinant viral vector is administered to a human subject as an active ingredient of the vaccine or pharmaceutical composition, the dosage of the recombinant virus or MVA may be administered in an amount approximately corresponding to $10^2$ to $10^{14}$ PFU, preferably $10^5$ to $10^{12}$ PFU, and more preferably $10^6$ to $10^{10}$ PFU per patient, calculated as the PFU of the recombinant virus.

In further aspects, when a recombinant viral vector is administered to a subject as an active ingredient of the vaccine or pharmaceutical composition, the dosage may be selected from a wide range in terms of the amount of expressible DNA introduced into the vaccine host or the amount of transcribed RNA. The dosage also depends on the strength of the transcription and translation promoters used in any transfer vectors used.

In some embodiments, the vaccine composition or pharmaceutical composition described herein may be administered by directly injecting a recombinant viral vector suspension prepared by suspending the recombinant virus or MVA in PBS (phosphate buffered saline) or saline into a local site (e.g., into the lung tissue, liver, muscle or brain), by nasal or respiratory inhalation, or by intravascular (i.v.) (e.g., intra-arterial, intravenous, and portal venous), subcutaneous (s.c.), intracutaneous (i.c.), intradermal (i.d.), or intraperitoneal (i.p.) administration. The vaccine or pharmaceutical composition of the present invention may be administered more than once. More specifically, after the initial administration, one or more additional vaccinations may be given as a booster. One or more booster administrations can enhance the desired effect. After the administration of the vaccine or pharmaceutical composition, booster immunization with a pharmaceutical composition containing the recombinant virus or MVA as described herein may be performed.

The following examples are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

Examples

Example 1: Materials and Methods

Viruses and cells: Baby hamster kidney (BHK-21) cells, chicken embryo fibroblasts (CEF), ARPE-19 EC, and MRC-5 FB were maintained and propagated as described previously (56, 57, 60). BHK-21, ARPE-19, and MRC-5 cells were obtained from the American Type Culture Collection (ATCC CCL-10 and ATCC CRL-2302). Chicken anemia virus-negative CEF cells were purchased from Charles River (Order Nr. 1010087). MVA 1974/NIH clone 1 and Fowl pox virus HP1.441 were kindly provided by Bernard Moss (NIAID) (33). HCMV TB40/E expressing green fluorescent protein (GFP) was reconstituted from TB40/E BAC, a kind gift from Christian Sinzger (Ulm University, Germany) (41, 44). For generating MVA stocks, MVA was propagated in BHK cells and purified through 36% sucrose density ultracentrifugation, then resuspended in 1 mM Tris-buffered saline and stored at −80° C. (56, 57). Titer of MVA stocks were determined on BHK cells by immunostaining of viral foci 18-24 after infection using rabbit polyclonal antibodies to vaccinia virus. TB40/E stocks were produced following virus propagation in ARPE-19 cells as described (60). Briefly, 70-90% confluent ARPE-19 cells were infected with TB40/E at 0.1 multiplicity of infection (MOI) and re-seeded weekly until 90-100% of cells were infected as monitored by GFP expression. Virus particles were concentrated from clarified medium by ultracentrifugation at 70,000×g over 20% sucrose (wt/vol) in Tris-buffered saline (0.1 M Tris-Cl [pH 7.4], 0.1 M NaCl). Concentrated virus was resuspended in Tris-buffered saline and stored at −80° C. Virus titration was performed by adding serial dilutions of the virus to ARPE-19 EC and by immunostaining for immediate early-1 protein (1E1) after 48 h of incubation (60).

Antibodies: Mouse monoclonal antibodies (MAb) 1B2, 54E11, 13B5, and 62-11 as well as peptide-specific rabbit polyclonal antisera to the individual PC subunits were generated previously (7, 60). Rabbit polyclonal antibodies to vaccinia virus that were used for MVA titration were purchased from LSBio (LS-C103289). MAb specific for HCMV 1E1 (p63-27) or gH (AP86) were kindly provided by Bill Britt (University of Alabama at Birmingham) (2, 43). Hybridoma supernatants of UL128 specific mouse monoclonal antibody Z9G11 was a gift from Giuseppe Gerna (*Pavia* University, Italy) (18). MAb 19C2 specific for the vaccinia BR5 protein was a kind gift from Bernard Moss (NIAID) (42).

Plasmids: Transfer plasmids for inserting BAC sequences into MVA by homologous recombination or PC subunits into MVA BAC by En passant mutagenesis (8, 48, 62), were generated using standard molecular biology cloning techniques. For inserting BAC sequences into the MVA Thymidine kinase (TK) gene by homologous recombination, a transfer vector was generated in which pBeloBAC11 sequences—including mini-F replicon, loxP site, and cos sequences—and a GFP expression cassette with vaccinia P11 late promoter were flanked by DNA sequences homologues to the MVA TK gene locus, as shown in FIG. 1. The pBeloBAC11 vector was obtained from New England Biolabs. TK homology flanks were derived by PCR amplification of genomic DNA sequences of MVA 1974/NIH clone 1 that corresponded to base pairs 69313-70000 and 70001-70703 of MVA strain Acambis (Accession Nr. AY603355.1). The GFP marker with P11 promoter was derived by PCR amplification from plasmid pLW73 (63). A unique AvrII restriction site was introduced between the ends of the TK homology flanks to allow linearization of the entire transfer construct, as shown in FIG. 1. For inserting the HCMV PC subunits either all together into only one insertion site or into two separate insertion sites of MVA-BAC DNA by En passant mutagenesis (48), plasmid pGEM-T-mH5 was used as a vector backbone to generate three different transfer constructs that comprised codon-optimized, P2A-linked PC subunit subsets of either UL128/130/131A (#1), gH/gL (#2) or gH/gL with an additional P2A sequence preceding the gH gene sequence (#3) (62). Generating a transfer vector comprising P2A-linked sequences of all five PC subunits was not successful. Each of the PC subunit subsets within the different transfer vectors were flanked upstream with Kozak and vaccinia mH5 promoter sequences and downstream with a vaccinia transcription termination signal (TTTTTAT, SEQ ID NO: 6) (62). In addition, kanamycin expression cassettes with adjacent I-SceI homing endonuclease restriction sites and flanking 50 bp gene duplications were introduced into the PC subunit subsets to allow En passant-mediated BAC insertion (48, 62). Codon-optimized, P2A-linked DNA sequences of the PC subunit were generated by taking advantage of the GenPlus Economy Synthesis Service from Genescript. All PC subunit gene sequences were based on HCMV strain TB40/E (TB40/E-BAC; Accession Nr. EF999921) (44), which were codon-optimized for vaccinia virus using the online Codon Optimization Tool from Integrated DNA Technologies (IDT). While retaining vaccinia codon usage, codon-optimized PC gene sequences were silently mutated to remove runs of more than three nucleotides of the same type in a row that are known to cause instability within heterologous DNA sequences inserted into MVA (63). Gene internal Kanamycin/I-SceI cassettes flanked by 50 bp gene duplications were generated by PCR amplification of plasmid pEPkan-S using primers that provided 50 bp gene duplications, and insertion of the resulting PCR products into unique restriction sites within the PC subunit gene sequences (49). For inserting mRFP expression cassettes into MVA-BAC DNA, an mRFP transfer construct for En passant mutagenesis was generated within the pGEM-T-mH5 vector analogous to the transfer constructs for the PC subunits. The mRFP gene sequence with internal kanamycin expression cassette and a 50 bp gene duplication was derived by PCR amplification of pEP-mRFP-in (49). Detailed sequence maps generated by Vector NTI (Invitrogen) for all plasmids are available. All transfer constructs were confirmed by sequencing.

BAC construction: Construction of the novel MVA-BAC with vector sequences inserted into the TK gene locus, termed MVA-BAC$^{TK}$, was generated by using a procedure similar to that described previously by Domi and colleagues (13). Briefly, 70-90% confluent CEF cells were infected with MVA 1974/NIH clone 1 at 0.01 MOI and after 2 h of incubation transfected with 2 µg of AvrII-linearized BAC transfer vector using Fugene HD transfection reagent (Roche) according to the manufacturers instruction. MVA recombinants were isolated following six rounds of plaque purification on CEF cells using GFP expression of the inserted BAC vector as a marker. CEF cells (70-90% confluent) were then infected with the isolated MVA recombinants at 5 MOI. After 2 h of incubation, the infected cells were incubated in growth medium containing 45 µM Isatin-β-thiosemicarbazone (IβT) to inhibit viral hairpin resolution and to promote heat-to-tail genome concatemerization and circularization (13). Plasmid transfection of pCICre expressing Cre recombinase that could have potentially enhanced genome circularization by recombination of loxP sites within the BAC sequences was not employed due to unfavorable findings made for MVA BAC generation by others previously (8, 13). After 5 h of incubation in presence of IβT, DNA was isolated from the infected CEF cells using the DNAeasy Blood and Tissue genome isolation Kit from Qiagen according to the manufacturer's instructions, and purified DNA was transformed into DH10B *E. coli* cells (MAX Efficiency DH10B Competent Cells, Invitrogen).

BAC mutagenesis: HCMV PC subunit subsets and mRFP expression cassettes were inserted into MVA-BAC DNA by En passant mutagenesis in GS1783 bacteria cells as described previously (48, 62). Briefly, transfer constructs for the HCMV and mRFP gene sequences as described above were amplified with primers containing 50 bp extensions homologous to target site (primers shown in Table 1), and inserted into the MVA genome via an initial Red recombination.

TABLE 1

| Primer pairs for recombination (5' to 3')[1] | Target site[2] | Genome position[3] |
|---|---|---|
| AAAAAATATATTATTTTTATGTTATTTTGTTAAAAATAATCATCGAATACGAACTAGTATAAAAAGGCGCGCC (SEQ ID NO: 7)<br>GAAGATACCAAAATAGTAAAGATTTTGCTATTCAGTGGACTGGATGATTCAAAAATTGAAAATAAATACAAAGGTTC (SEQ ID NO: 8) | Del2 | 20721 |
| AATTGTACTTTGTAATATAATGATATATATTTTCACTTTATCTCATTTGATTTTTATAAAAATTGAAAATAAATACAAAGGTTC (SEQ ID NO: 9)<br>ATTCCGAAATCTGTACATCATGCAGTGGTTAAACAAAAACATTTTTATTCCTAGTATAAAAAGGCGCGCC (SEQ ID NO: 10) | 64/65 | 56741 |
| ATATGAATATGATTTCAGATACTATATTTGTTCCTGTAGATAATAACTAAAAATTTTTATCTAGTATAAAAAGGCGCGCC (SEQ ID NO: 11)<br>GGAAAATTTTTCATCTCTAAAAAAAGATGTGGTCATTAGAGTTTGATTTTTATAAAAATTGAAAATAAATACAAGGTTC (SEQ ID NO: 12) | 69/70 | 63812 |
| TTGGGGAAATATGAACCTGACATGATTAAGATTGCTCTTTCGGTGGCTGGTAAAAAATTGAAAATAAATACAAAGGTTC (SEQ ID NO: 13)<br>ACAAAATTATGTATTTTGTTCTATCAACTACCTATAAAACTTTCCAAATACTAGTATAAAAAGGCGCGCC (SEQ ID NO: 14) | Del3 | 149341 |
| GGTTTATTGGATTCGTGTAATCATATATTTTGCATAACATGCATCATTTTTATAAAAATTGAAAATAAATACAAAGGTTC (SEQ ID NO: 15)<br>ACAATTATCCGACGCACCGGTTTCTCTTCGTGTTCTATGCCATATATTGATTTTTATCTAGTATAAAAAGGCGCGCC (SEQ ID NO: 16) | 7/8 | 12802 |
| GAATATGACTAAACCGATGACCATTTAAAAACCCCTCTCTAGCTTTCACTAAAAATTGAAAATAAATACAAAGGTTC (SEQ ID NO: 17)<br>ATAATGTTTTTATATTATACATGTTCTAAAAGAATAATCGATACAGTTTACTAGTATAAAAAGGCGCGCC (SEQ ID NO: 18) | 44/45 | 37330 |
| GTTCGCGGCTAATCGCGATAATGTAGCTTCTAGACTTTTGTCCTAATTTTTATAAAAATTGAAAATAAATACAAAGGTTC (SEQ ID NO: 19)<br>CTGGACGACACGGATTTATTAATATCGAAAAGGATATAATTGTATTTTAGTTTTTATCTAGTATAAAAAGGCGCGCC (SEQ ID NO: 20) | 47/48 | 38924 |
| ATCTAATGGATAAACTGAATCTAACAAAGAGCGACGTACAACTGTTGTAATTTTTATCTAGTATAAAAAGGCGCGCC (SEQ ID NO: 21)<br>CTTTGAAAGAATGTTTGGTTCAAAACCTACATTTTACGAAGCATAATTTTTATAAAAATTGAAAATAAATACAAGGTTC (SEQ ID NO: 22) | 55/56 | 48516 |
| GTTGTTGGCGTTGGTGGCGCTAGTCATCACATTAACTATTTTTATTACTTTATACTATAATTTTTATAAAATTGAAAATAAATACAAAGGTTC (SEQ ID NO: 23)<br>TTATGGCAGGTGAGATGTTTGTTAGAAGTCAGTCTAGTACTATTATAGTATAATTTTTATCTAGTATAAAAAGGCGCGCC (SEQ ID NO: 24) | 81/82 | 72908 |

TABLE 1-continued

| Primer pairs for recombination (5' to 3')[1] | Target site[2] | Genome position[3] |
|---|---|---|
| ATAAGATATCTTCTCAAAAGATCAAGGAAATGGAAGAAACAGAAGACTTTTAATTTTTATCTAGTATAAAAAG GCGCGCC (SEQ ID NO: 25) GTTTAAAAGACAGATCATAGAAAAATATGTTATTGATAAGAATTAATTTTTATAAAAATTGAAAATAAATACA AAGGTTC (SEQ ID NO: 26) | 90/91 | 82067 |
| GTTATTTTATGTCACCGCATTGGTGTTCCGATTTTAGTAATATGGAATAGTTTTTATCTAGTATAAAAGGCG CGCC (SEQ ID NO: 27) GCTGTTATGGTTCCTTACAGGAACATTCGTTACCGCATTTATCTAATTTTTATAAAAATTGAAAATAAATACA AAGGTTC (SEQ ID NO: 28) | 92/93 | 83162 |
| AGGATGTTATTACGAATCATTAAAAAAATTAACTGAGGATGATTGATTTTTATAAAAATTGAAAATAAATACA AAGGTTC (SEQ ID NO: 29) ACAATCCCGTTATAAAAATACACGATGGTAAATTAATTTATATTTTCTAATTTTTATCTAGTATAAAAGGCG CGCC (SEQ ID NO: 30) | 107/108 | 100231 |
| TCCATCTAGACTATATTATCAAAATTTGGAAACTTCAAAAACGATATTAGTTTTTATCTAGTATAAAAGGCG CGCC (SEQ ID NO: 31) AGACTTGATTGTGACATTTAGAGAACGATATTCGTATAAATTCTAATTTTTATAAAAATTGAAAATAAATACA AAGGTTC (SEQ ID NO: 32) | 116/117 | 109461 |
| ATTGTTTATACTCAAGATATTCGTTAAACGAATTAAAATTATTTAATTTTTATAAAAATTGAAAATAAATACA AAGGTTC (SEQ ID NO: 33) AGGAACAGATTAATCCAGACGATTGTTGTCTGGATATGGGAATGTATTAATTTTTATCTAGTATAAAAGGCG CGCC (SEQ ID NO: 34) | 122/123 | 117576 |
| GTTACCTCCGCAGTTTTTACGAGCGATTTCACGTTCAGCCTTCATGCGTCTTTTTATCTAGTATAAAAGGCG CGCC (SEQ ID NO: 35) GTGACAGAAGCTAAACCCGATAACGATAAGCGAATTCATGCTATAATTTTTATAAAAATTGAAAATAAATACA AAGGTTC (SEQ ID NO: 36) | Del6 | 129963 |
| ATTGATAATATAAATATGAGCATTAGTATTTCTGTGGATTAATAGATTTTTATAAAAATTGAAAATAAATACA AAGGTTC (SEQ ID NO: 37) TTATGAGGTATTTAGAGATTAGAGATGATTAATGATCCCCATACTAGAAATTTTTATCTAGTATAAAAGGCG CGCC (SEQ ID NO: 38) | 148/149 | 137500 |

[1]Undelined sequences indicate 5' primer extensions that mediated recombination.
[2]Recombination target sites given either as MVA deletion sites (Del2, Del3, and Del6) or as intergenic regions between the indicated ORFs of MVA (Accession Nr. U94848).
[3]Recombination insertion position within the MVA genome (Accession Nr. U94848).

Subsequently, the kanamycin marker within the gene sequences was seamlessly removed by a second Red recombination utilizing the engineered 50 bp gene duplications flanking the marker sequences (49, 62). For inserting P2A-linked PC subunits into two separate MVA insertion sites (MVA$^{TK}$-PC2A2), the UL128/130/131A and gH/gL subunit subsets were successively inserted by two subsequent En passant reactions into the MVA Deletion 2 site (Del2) and the intergenic region between MVA genes 69 and 70 (IGR69/70; Accession Nr. U94848), respectively. For inserting the PC subunits all together into only one insertion site (MVA$^{TK}$-PC2A1 and MVA$^{Del3}$-PC2A1), the UL128/130/131A subunits were inserted into the IGR69/70 by a first En passant mutagenesis reaction, and the gH/gL subunits were subsequently inserted into the UL128/130/131A-containing IGR69/70 site by a second En passant recombination reaction. All sequences inserted into the MVA-BAC DNA and sequences that mediated recombination were verified by sequencing. Detailed sequence maps are available for all engineered recombinant MVA-BAC constructs.

Virus reconstitution: Virus reconstitution from BAC DNA was performed as previously described (8, 60). Briefly, BHK cells were seeded at 1×10$^5$ cells per well in a six well plate and 16-20 h later transfected with ~2-4 µg of BAC DNA that was prepared from E. coli by alkaline lysis (4). Transfection was performed using X-tremeGENE HP DNA transfection reagent (Roche) according to manufacturer's instructions. Four hours post-transfection, BHK cells were infected with FPV at 0.1 MOI to initiate virus transcription. Virus reconstitution was monitored by GFP expression of the BAC vector, and transfected BHK cells were re-seeded in a 1:2 ratio until 100% of cells were infected.

Western Blot: Immunoblot detection of the HCMV PC subunits expressed from the MVA recombinants was performed by standard procedures. Briefly, 80-90% confluent BHK cells were infected with the MVA recombinants at MOI 5 and grown overnight for 16-20 h. Infected cells were harvested, clarified from cell debris by centrifugation at 300×g, and lysed in SDS sample buffer (2% SDS, 100 mM dithiothreitol [DTT], and 125 mM Tris-HCl [pH 8.8]). Proteins were boiled, electrophoretically separated by SDS-PAGE, and blotted to a PVDF membrane. HCMV gL and UL131A were detected with rabbit polyclonal antisera diluted 1/3000; UL128 and gH were detected with anti-HCMV UL128 MAb Z9G11 or gH MAb AP86 at a final concentration of 0.1 and 10 µg/ml, respectively; and UL130 and vaccinia BR5 were detected by using hybridoma supernatants diluted 1/10. Proteins were visualized with secondary antibodies (anti-rabbit or anti-mouse IgG antibody, Sigma) coupled to horseradish peroxidase (HRP) and chemiluminescence detection (Pierce ECL WB substrate, Pierce).

Flow Cytometry: Cell surface Flow cytometry staining to detect HCMV PC subunits expressed from the different MVA vectors by PC-specific NAb was performed as described previously (7). Briefly, BHK-21 (70-90% confluent) were infected with the MVA vectors at MOI 5. At 4 h post infection, infected cells were collected, washed in phosphate buffered saline (PBS), and incubated for 1 h at 4°

C. with 10 μg/ml NAb. After washing with PBS, the cells were incubated with Alexa Fluor 647 goat anti-mouse IgG (Life Technologies) at a dilution of 1:2,000. The cells were washed again and resuspended in PBS with 0.1% bovine serum albumin (BSA). Fifteen thousand events were collected using a Gallios flow cytometer (Beckman Coulter) and analyzed with FlowJo software (Tree Star).

Replication Kinetics: Multi-step replication kinetics to investigate the growth properties of MVA-BAC$^{TK}$-derived virus (MVA$^{TK}$) in comparison to wild-type MVA (MVA$^{WT}$; MVA 1974/NIH clone 1) was performed as follows. CEF cells of 70-90% confluency seeded in 6-well plates were infected in duplicate-wells per virus and per harvesting time point with either MVA$^{TK}$ or MVA$^{WT}$ at 0.05 MOI and harvested every 12 h for a period of 72 h. Collected cells were resuspended in 1 ml of Minimum Essential Medium (Corning) containing 2% Fetal bovine albumin. Virus was released from infected cells by standard thaw/freeze and sonication techniques. Virus prepared from each well and inoculum virus used to infect the CEF cells (time point 0) were titrated on BHK cells in duplicates to determine the titer for each time point based on four independent counts of viral foci per virus and per time point.

BAC sequencing: Sequencing of MVA-BAC$^{TK}$ (#1-81) was performed by Illumina sequencing at the Integrative Genomics Core Services of the City of Hope. MVA-BAC$^{TK}$ DNA (250 ng) was fragmented by using Covaris S220 with the 300 bp peak setting. The fragmented DNA was end-repaired and ligated to Illumina adaptor oligonucleotides with TruSeq DNA LT Sample Prep kit (Illumina). Ligation products were purified with 1.0×Ampure XP beads (Beckman Coulter). The purified products were used for cluster generation on cBot cluster generation system with HiSeq PE Cluster Kit V3 (Illumina). Sequencing run was performed in the paired end mode of 101 cycles of read 1, 7 cycles of index read and 101 cycles of read 2 using HiSeq2500 platform with HiSeq SBS Kit V3 (Illumina). Real-time analysis (RTA) 2.2.38 software was used to process the image analysis and base calling.

Mouse immunization: The Institutional Animal Care and Use Committee (IACUC) of the Beckman Research Institute of City of Hope approved protocol 98004 assigned for this study. All study procedures were carried out in strict accordance with the recommendations in the Guide for the Care and Use of Laboratory Animals and the Public Health Service Policy on the Humane Care and Use of Laboratory Animals. Methods of euthanasia followed "Report of the AVMA Panel on Euthanasia" (avma.org/kb/policies/documents/euthanasia.pdf). BALB/c mice (Jackson Laboratory) were vaccinated twice in three weeks interval via intraperitoneal (i.p.) route with 5×10$^7$ PFU of MVA. Blood samples for determining serum NAb titers were collected by eye bleed.

Neutralization assay: HCMV microneutralization assay was performed similar to published reports (7, 60). Heat-inactivated sera were serially two-fold diluted in 100 μl volumes using complete growth medium for ARPE-19 EC or MRC-5 FB depending on the cell type used in the assay. Dilutions ranged from 1:25 to 1:102400. Diluted serum was mixed with 100 μl of complete growth medium containing approximately 2400 PFU of HCMV TB40/E. After 2 h incubation, virus/sera mixtures were added in triplicate (50 μl) to ARPE-19 or MRC-5 cells seeded the day before at 1.5×10$^4$ cells/well in a clear bottom polystyrene 96-well plate (Corning) that contained 50 μl per well of complete growth medium. Cells were grown for 48 h and fixed in methanol/acetone. Infected cells were identified by immunostaining using mouse anti-HCMV 1E1 Ab (p63-27) and the Vectastain ABC kit (VectorLabs). The substrate was 3, 3'-diaminobenzidine (DAB, VectorLabs). Plates were analyzed by an automated system using the Axio Observer Z1 inverted microscope equipped with a linear motorized stage (Carl Zeiss). 1E1 positive nuclei were counted using ImagePro Premier (Media Cybernetics). For each dilution the average number of positive nuclei in triplicate was calculated. The percent neutralization titer (NT) for each dilution was calculated as follows: NT=[1-(positive nuclei number with immune sera)/(positive nuclei number with pre-immune sera)]×100. The titers that gave 50% neutralization (NT50) were calculated by determining the linear slope of the graph plotting NT versus plasma dilution by using the next higher and lower NT values that were closest to 50% neutralization.

Statistics: GraphPad Prism software version 5.0 (GraphPad) was used to compare NAb titers in the different vaccine groups by statistical analysis using Wilcoxon matched-pairs test.

Example 2: Construction of a Novel MVA-BAC, Termed MVA-BAC$^{TK}$

BAC clones of large viral genomes are powerful tools to generate recombinant virus by highly-efficient and versatile bacterial-based mutagenesis techniques (46). For MVA, two different BAC clones have been described (8, 35). One of these BAC, the original MVA-BAC generated by Cottingham and colleagues (8), has formed the basis for a previously introduced vaccine concept to stimulate high-titer HCMV NAb in mice and RM based on co-expression of all five PC subunits from a single MVA vector, termed MVA-PC (60). For generating the original MVA-BAC, BAC vector sequences were introduced into the MVA deletion 3 site (Del3), a commonly used insertion site for stable maintenance of heterologous DNA sequences (34). To distinguish this BAC from the newly developed MVA-BAC (MVA-BAC$^{TK}$), the original BAC clone is referred to as MVA-BAC$^{Del3}$, and virus reconstituted from this BAC is designated with MVA$^{Del3}$. Accordingly, MVA-PC will be designated herein as MVA$^{Del3}$-PC to refer to its origin from the original MVA-BAC$^{Del3}$ (60). The strategy disclosed herein to develop a novel MVA-BAC, termed MVA-BAC$^{TK}$, is based on introduction of the BAC vector into the MVA TK gene locus to retain MVA Del3 and other commonly used insertion sites (Del2, IGR64/65, IGR69/70 (32, 34, 63) accessible for transgene insertion while providing the option to generate a seamless self-excisable BAC vector within the TK gene sequence using techniques as described previously (10, 47, 61). Based on a procedure recently introduced for the generation of a vaccinia virus BAC by Domi and colleagues (13), pBeloBAC11 vector sequences together with a GFP expression cassette were inserted into the TK gene of the MVA genome by homologous recombination in CEF cells, and circularized genomes of plaque purified BAC recombinant virus were transformed into DH10B E. coli cells, as shown in FIG. 1. PCR and restriction enzyme digestion were used to identify clones potentially harboring full-length MVA genomes with BAC sequences inserted at the TK gene. Some of these BAC clones were additionally tested for MVA reconstitution in BHK cells to support the integrity of the cloned MVA genomes. One BAC clone (#1-81) was ultimately selected as MVA-BAC$^{TK}$.

Example 3 Characterization of MVA-BAC$^{TK}$

Figure 1B:
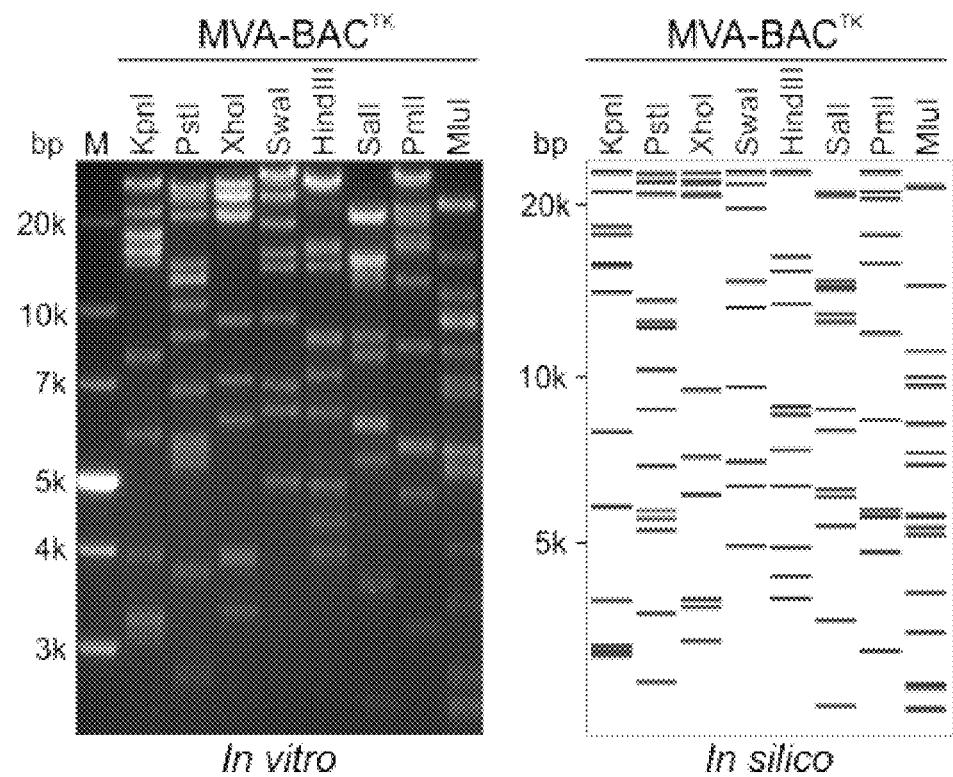
Figure 1C:
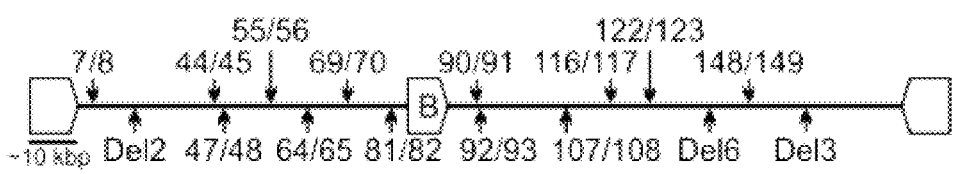
Figure 1D:
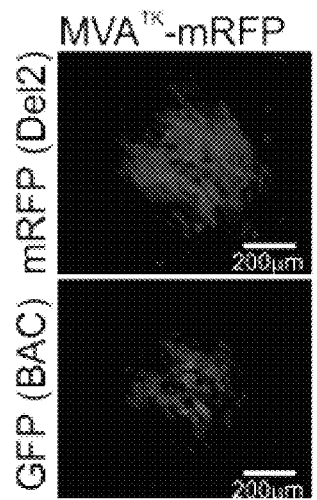
Figure 1E:
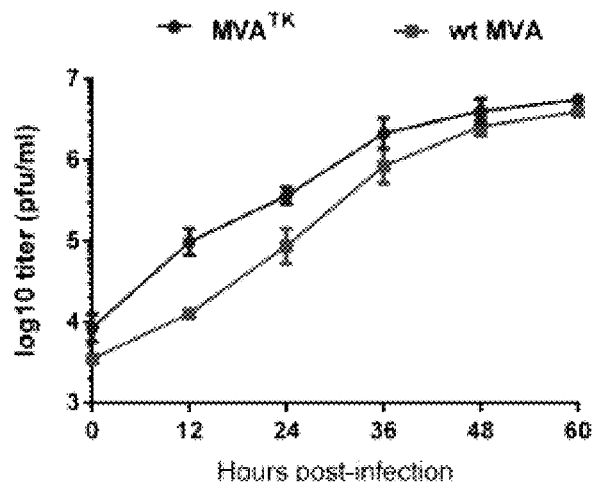

To further evaluate the integrity of the cloned MVA genome of MVA-BAC$^{TK}$ (#1-81), MVA-BAC$^{TK}$ DNA was investigated by extensive restriction pattern analysis and MVA-BAC$^{TK}$-derived virus (MVA$^{TK}$) by multi-step growth kinetics in BHK cells. As shown in FIG. 1B, BAC restriction pattern observed for MVA-BAC$^{TK}$ in vitro were comparable to those predicted for MVA-BAC$^{TK}$ in silico using Vector NTI. In addition, MVA$^{TK}$ showed replication kinetics in BHK cells that were similar to those of wtMVA 1974/NIH clone 1 (FIG. 1E). Note that overall slightly lower virus titers were observed for wtMVA than for MVA$^{TK}$, which was most likely a result of the slightly lower amounts of inoculum virus of wtMVA compared to MVA$^{TK}$. Based on these findings, the complete MVA-BAC$^{TK}$ #1-81 was sequenced by shotgun sequencing at 4000-fold coverage, resulting in a single sequence contig (excluding the flanking MVA repeat regions), and the sequence of the cloned genome of MVA-BAC$^{TK}$ was found to be identical to the genome sequence of MVA strain Acambis (Accession Nr. AY603355.1). Finally, to evaluate whether MVA-BAC$^{TK}$ allowed to generate virus recombinants, MVA-BAC$^{TK}$ was transferred to GS1783 E. coli cells that support En passant mutagenesis, a highly-efficient and versatile BAC manipulation procedure (10, 48). Using this technique, an mRFP expression cassette was introduced into 12 different commonly and non-commonly used insertion sites at different positions of the MVA genome (FIG. 1C). As summarized in Table 1, virus expressing mRFP— and GFP of the BAC vector (FIG. 1D)— was reconstituted in BHK cells by all engineered BAC recombinants.

In sum, these results indicate that MVA-BAC$^{TK}$ comprises a full-length, intact genomic clone of MVA that allows to reconstitute replication-competent and to efficiently generate virus recombinants.

Example 4: Construction of MVA expressing P2A-cleavable HCMV PC subunits

MVA$^{Del3}$-PC was generated by introducing each of the five PC subunits with its own mH5 promoter into a different commonly used MVA insertion site (Del2, Del3, IGR64/65, IGR69/70; FIG. 1C) to allow equal and high-level expression of the PC subunits while minimizing the potential risk of intra- or intermolecular homologous recombination between promoter elements (60, 62). Because of the separate insertion of the PC subunits, occupancy of commonly used insertion sites, and multiple mH5 promoter elements, insertion of additional HCMV antigens into MVA$^{Del3}$-PC might render the vector unstable or replication incompetent. To address this issue, the ribosomal skipping mechanism mediated by 2A peptides to express polycistronic PC subunits from only one or two MVA insertion sites was exploited (45). Of the different, commonly used 2A peptide sequences, the 2A peptide of porcine teschovirus-1 (P2A) has been shown recently to mediate most effective cleavage of 2A-linked polyproteins (24). Therefore, to allow efficient and equal processing of all five PC subunits and, hence, potentially their stoichiometric expression, all signals linking the PC subunits were based on P2A peptides. To prevent instability by homologous recombination of the P2A ribosomal skipping signals, four different DNA sequences with varying codon usage were used to encode P2A peptides linking different PC subunits (FIG. 2B). Using En passant-mediated mutagenesis of MVA-BAC$^{TK}$, codon-optimized, P2A-linked DNA sequences of the five PC subunits were inserted either all together into the IGR69/70 insertion site for generating MVA expressing self-cleavable polyproteins composed of all five PC subunits (MVA$^{TK}$-PC2A1, FIG. 2A), or separately as subunit subsets into the Del2 and IGR69/70 insertion sites to generate MVA co-expressing self-processing polyproteins composed of UL128/130/131A and gH/gL (MVA$^{TK}$-PC2A2, FIG. 2A). While both insertion sites have been described to allow stable transgenes insertion, the G1 L/I8R insertion site is known to promote stable propagation of especially large sequences or antigens with potential cellular toxicity such as transmembrane proteins (53). For comparing NAb induction by self-processing PC subunits of virus derived from MVA-BAC$^{TK}$ and the original MVA-BAC$^{Del3}$, MVA with all five PC subunits inserted into IGR69/70 using MVA-BAC$^{Del3}$ (MVA$^{Del3}$-PC2A1) was also generated, which was analogously constructed to MVA$^{TK}$-PC2A1 (FIG. 2A).

Example 5: Expression and Cleavage of P2A-Linked HCMV PC Subunits Encoded by MVA To characterize the expression and cleavage of the P2A-linked HCMV PC subunits expressed from the polycistronic MVA vectors (MVA$^{TK}$-PC2A1, MVA$^{TK}$-PC2A2, and MVA$^{Del3}$-PC2A1), Immunoblot analysis was used to detect the PC subunits in whole cell lysates of BHK cells infected with the different MVA vectors. As controls, MVA$^{Del3}$-PC and MVA$^{Del3}$-gB were included in the Immunblot analysis. As shown in FIG. 3, marked differences in expression of the PC subunits were observed for the different MVA vectors. While robust expression of all five PC subunits could be confirmed for MVA$^{TK}$-PC2A2 and control vector MVA$^{Del3}$-PC, expression of only four PC subunits (gH, gL, UL128, and UL130) could be verified for the pentacistronic vectors MVA$^{TK}$-PC2A1 and MVA$^{Del3}$-PC2A1. UL131A expression of MVA$^{TK}$-PC2A1 and MVA$^{Del3}$-PC2A1 could not be unambiguously verified due to high non-specific background using polyclonal antiserum for detection. Expression levels of the PC subunits were generally higher with MVA$^{TK}$-PC2A2 than with MVA$^{TK}$-PC2A1 and MVA$^{Del3}$-PC2A1. Highest expression levels of the PC subunits were observed with control vector MVA$^{Del3}$-PC when compared to any of the polycistronic vectors. This suggests that co-expression of P2A-linked UL128/130/131A and gH/gL subunits subsets from two separate insertion sites is more efficient than P2A-based polycistronic expression of all five PC subunits from only one MVA insertion site, and highest expression is achieved when all five PC subunits are inserted into separate MVA insertion sites. Notably, all PC subunits of the different MVA vectors were expressed by the same vaccinia promoter (mH5, FIG. 2).

Most of the detectable PC subunits of the three polycistronic MVA vectors had higher molecular weight than their counterparts expressed from MVA$^{Del3}$-PC due to the C-terminal P2A peptide remnants following cleavage of the PC subunits (FIG. 3). Only gH of all three polycistronic MVA vectors, and UL131A of MVA$^{TK}$-PC2 had similar molecular weights compared to their counterparts expressed from MVA$^{Del3}$-PC as they did not contain C-terminal P2A peptides due to their positioning at the 3' end of the polycistronic expression constructs. Importantly, protein bands of sizes higher than the approximate expected molecular weight of the PC subunits (~85 KDa for gH; ~35 KDa for gL; ~15 KDa for UL128; ~35 KDa for UL130; and ~18 KDa for UL131A) that would indicate incomplete P2A-mediated cleavage were not observed, suggesting that all HCMV PC of the polycistronic vectors were efficiently processed. The two protein bands of different molecular weight that were observed for UL128 and gL for all three polycistronic vectors appeared to represent immature and mature forms of UL128 or gL rather than incompletely cleaved subunits as the observed protein bands did not match products with molecular weight that would result from incomplete cleavage of the PC subunits. Proteins bands that were of lower molecular weight than the anticipated sizes of the PC subunits as for example observed for UL130 and gL of MVA$^{TK}$-PC2A2 and MVA$^{Del3}$-PC were most likely degradation products, though they may also have resulted from different expression or replication properties of the MVA vectors (FIG. 3).

In sum, these results indicate that the P2A-linked PC subunits expressed from the three polycistronic MVA vectors are efficiently cleaved, though MVA$^{TK}$-PC2A2 expresses all five HCMV PC subunits with higher efficacy than MVA$^{TK}$-PC2A1 and MVA$^{Del3}$-PC2A1.

Example 6: Cell Surface Detection of MVA-Expressed P2A-Linked PC Subunits by NAb A panel of PC-specific NAb from MVA$^{Del3}$-PC immunized mice that had antigen recognition pattern and neutralization potency similar to human NAb isolated from HCMV+individuals was recently isolated (7, 29). Two of these isolated NAb recognized quaternary conformational epitopes formed by UL128/130/131A (162) or UL130/131A (54E11), while two other NAb recognized epitopes constituted by UL128 (1365) or gH alone (62-11) (29). By taking advantage of these four existing NAb, it was investigated by cell surface Flow cytometry staining of MVA infected BHK cells whether the PC subunits expressed from the different polycistronic MVA vectors assembled into complexes and formed conformational and linear neutralizing epitopes. MVA$^{Del3}$-PC and MVA$^{Del3}$ expressing gB were included as controls in the Flow cytometry analysis. As shown in FIG. 4, BHK cells infected with either of the three polycistronic MVA vectors or control vector MVA$^{Del3}$-PC were efficiently stained with all four NAb. While the intensity of the BHK staining with all four NAb was generally comparable for all MVA vectors; slightly lower staining intensity was observed for the two pentacistronic vectors MVA$^{TK}$-PC2A1 and MVA$^{Del3}$-PC2A1 and slightly higher staining intensity was observed for MVA$^{TK}$-PC2A2 compared to MVA$^{Del3}$-PC.

In sum, these results provide evidence that the P2A-linked PC subunits expressed from all three polycistronic MVA vectors assemble efficiently and are transported to the cell surface as five-member protein complexes that present different conformational and linear neutralizing epitopes.

Example 7: NAb Induction by MVA Vectors Expressing P2A-Linked PC Subunits

In order to investigate whether the developed MVA vectors expressing P2A-linked PC subunits have ability to elicit HCMV specific NAb responses, NAb induction by the polycistronic MVA vectors in vaccinated Balb/c mice was evaluated. Groups of five or six Balb/c mice were vaccinated twice in three weeks interval with the MVA vectors, and HCMV specific NAb responses in mouse sera were measured against HCMV strain TB40/E on ARPE-19 EC and MRC-5 FB by microneutralization assay over a period of 6 months. A two-dose immunization schedule was chosen based on a recent observation that two immunizations with MVA$^{Del3}$-PC are sufficient to stimulate high-titer HCMV specific NAb in mice and RM (60). MVA$^{Del3}$-PC was included as control in the immunization study. All polycistronic MVA vectors expressing P2A-linked PC subunits and control vector MVA$^{Del3}$-PC stimulated comparable and potent EC and FB specific NAb responses that were consistent with those observed previously with MVA$^{Del3}$-PC in mice (60). Robust NAb responses were induced by all MVA vectors after only one immunization, and these responses were boosted in all vaccine groups to maximum titers after the second immunization. In addition, NAb remained relatively stable in all vaccine groups until the end of the experiment at week 24 after the booster immunization. Consistent with previous immunization studies based on the PC and with NAb responses found in HCMV+individuals, NAb induced by all MVA vectors that were measured on MRC-5 FB were significantly lower than those measured on ARPE-19 EC (11, 18, 23, 60). While EC specific NAb titers across all vaccine groups were generally comparable (except at week 24 comparing MVA$^{Del3}$-PC and MVA$^{Del3}$-PC2A1), FB specific NAb titers were generally slightly lower in the MVA$^{Del3}$-PC control vector group than in animal groups immunized with any of the polycistronic MVA vectors (except at week 24 comparing MVA$^{Del3}$-PC and MVA$^{TK}$-PC2A1). Notably, NAb responses that were measured in this study for control vector MVA$^{Del3}$-PC appeared slightly lower than those observed in mice with MVA$^{Del3}$-PC in previous studies (60).

In sum, these results indicate that all three MVA vectors expressing P2A-linked PC subunits (MVATKPC2A2, MVATKPC2A1, and MVA$^{Del3}$-PC2A1) have potent and comparable ability to elicit HCMV NAb responses in mice.

REFERENCES

The references, patents and published patent applications listed below, and all references cited in the specification above are hereby incorporated by reference in their entirety, as if fully set forth herein.

1. Adler, B., L. Scrivano, Z. Ruzcics, B. Rupp, C. Sinzger, and U. Koszinowski. 2006. Role of human cytomegalovirus UL131A in cell type-specific virus entry and release. The Journal of general virology 87:2451-2460.
2. Andreoni, M., M. Faircloth, L. Vugler, and W. J. Britt. 1989. A rapid microneutralization assay for the measurement of neutralizing antibody reactive with human cytomegalovirus. Journal of virological methods 23:157-167.
3. Bernstein, D. I., F. M. Munoz, S. T. Callahan, R. Rupp, S. H. Wootton, K. M. Edwards, C. B. Turley, L. R. Stanberry, S. M. Patel, M. M. McNeal, S. Pichon, C. Amegashie, and A. R. Bellamy. 2016. Safety and efficacy of a cytomegalovirus glycoprotein B (gB) vaccine in adolescent girls: A randomized clinical trial. Vaccine 34:313-319.
4. Birnboim, H. C., and J. Doly. 1979. A rapid alkaline extraction procedure for screening recombinant plasmid DNA. Nucleic acids research 7:1513-1523.
5. Butler, D. 2016. Zika raises wider birth-defect issue. Nature 535:17-17.
6. Carroll, M. W., and B. Moss. 1997. Host range and cytopathogenicity of the highly attenuated MVA strain of vaccinia virus: propagation and generation of recombinant viruses in a nonhuman mammalian cell line. Virology 238:198-211.
7 Chiuppesi, F., F. Wussow, E. Johnson, C. Bian, M. Zhuo, A. Rajakumar, P. A. Barry, W. J. Britt, R. Chakraborty, and D. J. Diamond. 2015. Vaccine-Derived Neutralizing Antibodies to the Human Cytomegalovirus gH/gL Pentamer Potently Block Primary Cytotrophoblast Infection. Journal of virology 89:11884-11898.
8. Cottingham, M. G., R. F. Andersen, A. J. Spencer, S. Saurya, J. Furze, A. V. Hill, and S. C. Gilbert. 2008. Recombination-mediated genetic engineering of a bacterial artificial chromosome clone of modified vaccinia virus Ankara (MVA). PloS one 3:e1638.
9. Cottingham, M. G., and M. W. Carroll. 2013. Recombinant MVA vaccines: dispelling the myths. Vaccine 31:4247-4251.
10. Cottingham, M. G., and S. C. Gilbert. 2010. Rapid generation of markerless recombinant MVA vaccines by en passant recombineering of a self-excising bacterial artificial chromosome. Journal of virological methods 168:233-236.
11. Cui, X., B. P. Meza, S. P. Adler, and M. A. McVoy. 2008. Cytomegalovirus vaccines fail to induce epithelial entry neutralizing antibodies comparable to natural infection. Vaccine 26:5760-5766.
12. de Felipe, P. 2004. Skipping the co-expression problem: the new 2A "CHYSEL" technology. Genetic vaccines and therapy 2:13.
13. Domi, A., and B. Moss. 2002. Cloning the vaccinia virus genome as a bacterial artificial chromosome in *Escherichia coli* and recovery of infectious virus in mammalian cells. Proceedings of the National Academy of Sciences of the United States of America 99:12415-12420.
14. Donnelly, M. L., G. Luke, A. Mehrotra, X. Li, L. E. Hughes, D. Gani, and M. D. Ryan. 2001. Analysis of the aphthovirus 2A/2B polyprotein 'cleavage' mechanism indicates not a proteolytic reaction, but a novel translational effect: a putative ribosomal 'skip'. The Journal of general virology 82:1013-1025.
15. Draper, S. J., M. G. Cottingham, and S. C. Gilbert. 2013. Utilizing poxviral vectored vaccines for antibody induction-progress and prospects. Vaccine 31:4223-4230.
16. Freed, D. C., Q. Tang, A. Tang, F. Li, X. He, Z. Huang, W. Meng, L. Xia, A. C. Finnefrock, E. Durr, A. S. Espeseth, D. R. Casimiro, N. Zhang, J. W. Shiver, D. Wang, Z. An, and T. M. Fu. 2013. Pentameric complex of viral glycoprotein H is the primary target for potent neutralization by a human cytomegalovirus vaccine. Proceedings of the National Academy of Sciences of the United States of America 110:E4997-5005.
17. Gerna, G., E. Percivalle, L. Perez, A. Lanzavecchia, and D. Lilleri. 2016. Monoclonal Antibodies to Different Components of the Human Cytomegalovirus (HCMV) Pentamer gH/gL/pUL128L and Trimer gH/gL/gO as well as Antibodies Elicited during Primary HCMV Infection Prevent Epithelial Cell Syncytium Formation. Journal of virology 90:6216-6223.
18. Gerna, G., A. Sarasini, M. Patrone, E. Percivalle, L. Fiorina, G. Campanini, A. Gallina, F. Baldanti, and M. G. Revello. 2008. Human cytomegalovirus serum neutralizing antibodies block virus infection of endothelial/epithelial cells, but not fibroblasts, early during primary infection. The Journal of general virology 89:853-865.
19. Gilbert, S. C. 2013. Clinical development of Modified Vaccinia virus Ankara vaccines. Vaccine 31:4241-4246.
20. Hahn, G., M. G. Revello, M. Patrone, E. Percivalle, G. Campanini, A. Sarasini, M. Wagner, A. Gallina, G. Milanesi, U. Koszinowski, F. Baldanti, and G. Gerna. 2004. Human cytomegalovirus UL131-128 genes are indispensable for virus growth in endothelial cells and virus transfer to leukocytes. Journal of virology 78:10023-10033.
21. Hofmann, I., Y. Wen, C. Ciferri, A. Schulze, V. Fuhner, M. Leong, A. Gerber, R. Gerrein, A. Nandi, A. E. Lilja, A. Carfi, and H. Laux. 2015. Expression of the Human Cytomegalovirus Pentamer Complex for vaccine use in a CHO system. Biotechnology and bioengineering.
22. Jiang, X. J., B. Adler, K. L. Sampaio, M. Digel, G. Jahn, N. Ettischer, Y. D. Stierhof, L. Scrivano, U. Koszinowski, M. Mach, and C. Sinzger. 2008. UL74 of human cytomegalovirus contributes to virus release by promoting secondary envelopment of virions. Journal of virology 82:2802-2812.
23. Kabanova, A., L. Perez, D. Lilleri, J. Marcandalli, G. Agatic, S. Becattini, S. Preite, D. Fuschillo, E. Percivalle, F. Sallusto, G. Gerna, D. *Corti*, and A. Lanzavecchia. 2014. Antibody-driven design of a human cytomegalovirus gHgLpUL128L subunit vaccine that selectively elicits potent neutralizing antibodies. Proceedings of the National Academy of Sciences of the United States of America 111:17965-17970.
24. Kim, J. H., S. R. Lee, L. H. Li, H. J. Park, J. H. Park, K. Y. Lee, M. K. Kim, B. A. Shin, and S. Y. Choi. 2011. High cleavage efficiency of a 2A peptide derived from porcine teschovirus-1 in human cell lines, zebrafish and mice. PloS one 6:e18556.
25. La Rosa, C., J. Longmate, J. Martinez, Q. Zhou, T. I. Kaltcheva, W. Tsai, J. Drake, M. Carroll, F. Wussow, F. Chiuppesi, N. Hardwick, S. Dadwal, I. Aldoss, R. Nakamura, J. A. Zaia, and D. J. Diamond. 2016. MVA vaccine encoding CMV antigens safely induces durable expansion of CMV-specific T-cells in healthy adults. Blood.
26. Lilleri, D., A. Kabanova, A. Lanzavecchia, and G. Gerna. 2012. Antibodies against neutralization epitopes of human cytomegalovirus gH/gL/pUL128-130-131 complex and virus spreading may correlate with virus control in vivo. Journal of clinical immunology 32:1324-1331.
27. Lilleri, D., A. Kabanova, M. G. Revello, E. Percivalle, A. Sarasini, E. Genini, F. Sallusto, A. Lanzavecchia, D. *Corti*, and G. Gerna. 2013. Fetal human cytomegalovirus transmission correlates with delayed maternal antibodies to gH/gL/pUL128-130-131 complex during primary infection. PloS one 8:e59863.
28. Loughney, J. W., R. R. Rustandi, D. Wang, M. C. Troutman, L. W. Dick, Jr., G. Li, Z. Liu, F. Li, D. C. Freed, C. E. Price, V. M. Hoang, T. D. Culp, P. A. DePhillips, T. M. Fu, and S. Ha. 2015. Soluble Human Cytomegalovirus gH/gL/pUL128-131 Pentameric Complex, but not gH/gL, Inhibits Viral Entry to Epithelial Cells and Presents Dominant Native Neutralizing Epitopes. The Journal of biological chemistry.
29. Macagno, A., N. L. Bernasconi, F. Vanzetta, E. Dander, A. Sarasini, M. G. Revello, G. Gerna, F. Sallusto, and A. Lanzavecchia. 2010. Isolation of human monoclonal antibodies that potently neutralize human cytomegalovirus infection by targeting different epitopes on the gH/gL/UL128-131A complex. Journal of virology 84:1005-1013.
30. Manghera, A., and G. R. McLean. 2016. Human cytomegalovirus vaccination: progress and perspectives of recombinant gB. Future virology 11:439-449.
31. Manicklal, S., V. C. Emery, T. Lazzarotto, S. B. Boppana, and R. K. Gupta. 2013. The "silent" global burden of congenital cytomegalovirus. Clinical microbiology reviews 26:86-102.
32. Manuel, E. R., Z. Wang, Z. Li, C. La Rosa, W. Zhou, and D. J. Diamond. 2010. Intergenic region 3 of modified vaccinia ankara is a functional site for insert gene expression and allows for potent antigen-specific immune responses. Virology 403:155-162.
33. Mayr, A., and K. Malicki. 1966. [Attenuation of virulent fowl pox virus in tissue culture and characteristics of the attenuated virus]. Zentralblatt fur Veterinarmedizin. Reihe B. Journal of veterinary medicine. Series B 13:1-13.
34. Meisinger-Henschel, C., M. Schmidt, S. Lukassen, B. Linke, L. Krause, S. Konietzny, A. Goesmann, P. Howley, P. Chaplin, M. Suter, and J. Hausmann. 2007. Genomic sequence of chorioallantois vaccinia virus Ankara, the ancestor of modified vaccinia virus Ankara. The Journal of general virology 88:3249-3259.
35. Meisinger-Henschel, C., M. Spath, S. Lukassen, M. Wolferstatter, H. Kachelriess, K. Baur, U. Dirmeier, M. Wagner, P. Chaplin, M. Suter, and J. Hausmann. 2010. Introduction of the six major genomic deletions of modified vaccinia virus Ankara (MVA) into the parental vaccinia virus is not sufficient to reproduce an MVA-like phenotype in cell culture and in mice. Journal of virology 84:9907-9919.
36. Mlakar, J., M. Korva, N. Tul, M. Popovic, M. Poljsak-Prijatelj, J. Mraz, M. Kolenc, K. Resman Rus, T. Vesnaver Vipotnik, V. Fabjan Vodusek, A. Vizjak, J. Pizem, M. Petrovec, and T. Avsic Zupanc. 2016. Zika Virus Associated with Microcephaly. The New England journal of medicine 374:951-958.
37. Pass, R. F. 2009. Development and evidence for efficacy of CMV glycoprotein B vaccine with MF59 adjuvant. Journal of clinical virology: the official publication of the Pan American Society for Clinical Virology 46 Suppl 4:S73-76.
38. Pereira, L., M. Petitt, A. Fong, M. Tsuge, T. Tabata, J. Fang-Hoover, E. Maidji, M. Zydek, Y. Zhou, N. Inoue, S. Loghavi, S. Pepkowitz, L. M. Kauvar, and D. Ogunyemi. 2014. Intrauterine growth restriction caused by underlying congenital cytomegalovirus infection. The Journal of infectious diseases 209:1573-1584.
39. Ryan, M. D., A. M. King, and G. P. Thomas. 1991. Cleavage of foot-and-mouth disease virus polyprotein is mediated by residues located within a 19 amino acid sequence. The Journal of general virology 72 (Pt 11): 2727-2732.
40. Ryckman, B. J., M. A. Jarvis, D. D. Drummond, J. A. Nelson, and D. C. Johnson. 2006. Human cytomegalovirus entry into epithelial and endothelial cells depends on genes UL128 to UL150 and occurs by endocytosis and low-pH fusion. Journal of virology 80:710-722.
41. Sampaio, K. L., Y. Cavignac, Y. D. Stierhof, and C. Sinzger. 2005. Human cytomegalovirus labeled with green fluorescent protein for live analysis of intracellular particle movements. Journal of virology 79:2754-2767.
42. Schmelz, M., B. Sodeik, M. Ericsson, E. J. Wolffe, H. Shida, G. Hiller, and G. Griffiths. 1994. Assembly of vaccinia virus: the second wrapping cisterna is derived from the trans Golgi network. Journal of virology 68:130-147.
43. Simpson, J. A., J. C. Chow, J. Baker, N. Avdalovic, S. Yuan, D. Au, M. S. Co, M. Vasquez, W. J. Britt, and K. L. Coelingh. 1993. Neutralizing monoclonal antibodies that distinguish three antigenic sites on human cytomegalovirus glycoprotein H have conformationally distinct binding sites. Journal of virology 67:489-496.
44. Sinzger, C., G. Hahn, M. Digel, R. Katona, K. L. Sampaio, M. Messerle, H. Hengel, U. Koszinowski, W. Brune, and B. Adler. 2008. Cloning and sequencing of a highly productive, endotheliotropic virus strain derived from human cytomegalovirus TB40/E. The Journal of general virology 89:359-368.
45. Szymczak, A. L., C. J. Workman, Y. Wang, K. M. Vignali, S. Dilioglou, E. F. Vanin, and D. A. Vignali. 2004. Correction of multi-gene deficiency in vivo using a single 'self-cleaving' 2A peptide-based retroviral vector. Nature biotechnology 22:589-594.
46. Tischer, B. K., and B. B. Kaufer. 2012. Viral bacterial artificial chromosomes: generation, mutagenesis, and removal of mini-F sequences. Journal of biomedicine & biotechnology 2012:472537.
47. Tischer, B. K., B. B. Kaufer, M. Sommer, F. Wussow, A. M. Arvin, and N. Osterrieder. 2007. A self-excisable infectious bacterial artificial chromosome clone of varicella-zoster virus allows analysis of the essential tegument protein encoded by ORF9. Journal of virology 81:13200-13208.
48. Tischer, B. K., G. A. Smith, and N. Osterrieder. 2010. En passant mutagenesis: a two step markerless red recombination system. Methods Mol Biol 634:421-430.
49. Tischer, B. K., J. von Einem, B. Kaufer, and N. Osterrieder. 2006. Two-step red-mediated recombination for versatile high-efficiency markerless DNA manipulation in *Escherichia coli*. BioTechniques 40:191-197.
50. Vanarsdall, A. L., P. W. Howard, T. W. Wisner, and D. C. Johnson. 2016. Human Cytomegalovirus gH/gL Forms a Stable Complex with the Fusion Protein gB in Virions. PLoS pathogens 12:e1005564.
51. Vanarsdall, A. L., and D. C. Johnson. 2012. Human cytomegalovirus entry into cells. Current opinion in virology 2:37-42.
52. Verheust, C., M. Goossens, K. Pauwels, and D. Breyer. 2012. Biosafety aspects of modified vaccinia virus Ankara (MVA)-based vectors used for gene therapy or vaccination. Vaccine 30:2623-2632.
53. Wagner, S., M. L. Bader, D. Drew, and J. W. de Gier. 2006. Rationalizing membrane protein overexpression. Trends in biotechnology 24:364-371.
54. Wang, D., D. C. Freed, X. He, F. Li, A. Tang, K. S. Cox, S. A. Dubey, S. Cole, M. B. Medi, Y. Liu, J. Xu, Z. Q. Zhang, A. C. Finnefrock, L. Song, A. S. Espeseth, J. W. Shiver, D. R. Casimiro, and T. M. Fu. 2016. A replication-defective human cytomegalovirus vaccine for prevention of congenital infection. Science translational medicine 8:362ra145.
55. Wang, D., and T. Shenk. 2005. Human cytomegalovirus virion protein complex required for epithelial and endothelial cell tropism. Proceedings of the National Academy of Sciences of the United States of America 102:18153-18158.
56. Wang, Z., C. La Rosa, R. Maas, H. Ly, J. Brewer, S. Mekhoubad, P. Daftarian, J. Longmate, W. J. Britt, and D. J. Diamond. 2004. Recombinant modified vaccinia virus Ankara expressing a soluble form of glycoprotein B causes durable immunity and neutralizing antibodies against multiple strains of human cytomegalovirus. Journal of virology 78:3965-3976.
57. Wang, Z., J. Martinez, W. Zhou, C. La Rosa, T. Srivastava, A. Dasgupta, R. Rawal, Z. Li, W. J. Britt, and D. Diamond. 2010. Modified H5 promoter improves stability of insert genes while maintaining immunogenicity during extended passage of genetically engineered MVA vaccines. Vaccine 28:1547-1557.
58. Wen, Y., J. Monroe, C. Linton, J. Archer, C. W. Beard, S. W. Barnett, G. Palladino, P. W. Mason, A. Carfi, and A. E. Lilja. 2014. Human cytomegalovirus gH/gL/UL128/UL130/UL131A complex elicits potently neutralizing antibodies in mice. Vaccine 32:3796-3804.
59. Wille, P. T., A. J. Knoche, J. A. Nelson, M. A. Jarvis, and D. C. Johnson. 2010. A human cytomegalovirus gO-null mutant fails to incorporate gH/gL into the virion envelope and is unable to enter fibroblasts and epithelial and endothelial cells. Journal of virology 84:2585-2596.
60. Wussow, F., F. Chiuppesi, J. Martinez, J. Campo, E. Johnson, C. Flechsig, M. Newell, E. Tran, J. Ortiz, C. La Rosa, A. Herrmann, J. Longmate, R. Chakraborty, P. A.

Barry, and D. J. Diamond. 2014. Human cytomegalovirus vaccine based on the envelope gH/gL pentamer complex. PLoS pathogens 10:e1004524.
61. Wussow, F., H. Fickenscher, and B. K. Tischer. 2009. Red-mediated transposition and final release of the mini-F vector of a cloned infectious herpesvirus genome. PloS one 4:e8178.
62. Wussow, F., Y. Yue, J. Martinez, J. D. Deere, J. Longmate, A. Herrmann, P. A. Barry, and D. J. Diamond. 2013. A vaccine based on the rhesus cytomegalovirus UL128 complex induces broadly neutralizing antibodies in rhesus macaques. Journal of virology 87:1322-1332.
63. Wyatt, L. S., P. L. Earl, W. Xiao, J. L. Americo, C. A. Cotter, J. Vogt, and B. Moss. 2009. Elucidating and minimizing the loss by recombinant vaccinia virus of human immunodeficiency virus gene expression resulting from spontaneous mutations and positive selection. Journal of virology 83:7176-7184.
64. Zhou, M., J. M. Lanchy, and B. J. Ryckman. 2015. Human cytomegalovirus gH/gL/gO promotes the fusion step of entry into all cell types whereas gH/gL/UL128-131 broadens virus tropism through a distinct mechanism. Journal of virology.

What is claimed is:

1. A pharmaceutical composition comprising:
   (i) one or more vectors, each vector comprising one or more expression cassette(s), each expression cassette comprising:
      a single promoter;
      two or more nucleic acid sequences that encode two or more herpesvirus glycoprotein complex subunits or antigenic fragments thereof, wherein the two or more herpesvirus glycoprotein complex subunits or antigenic fragments thereof, when expressed by the expression cassette, form a herpesvirus glycoprotein complex that is functional and effectively elicits neutralizing antibody responses, and wherein the two or more herpesvirus glycoprotein complex subunits or antigenic fragments thereof are derived from varicella-zoster virus (VZV), Epstein-Barr virus (EBV), Kaposi's Sarcoma-associated herpesvirus (KSHV), human herpesvirus 6 (HHV-6), human herpesvirus 7 (HHV-7);
      one or more 2A peptide signal sequences that mediate ribosomal skipping or one or more internal ribosomal entry sites between each of the two or more nucleic acid sequences;
      wherein the two or more herpesvirus glycoprotein complex subunits or antigenic fragments thereof are simultaneously expressed by the expression cassette;
      wherein the one or more vectors is (i) a plasmid or (ii) a viral vector selected from a CMV vector, a vaccinia vector, or an adenoviral vector; and
   (ii) a pharmaceutically acceptable carrier, adjuvant, additive or combination thereof.

2. The pharmaceutical composition of claim 1, wherein each vector further comprises a second expression cassette comprising:
   a second promoter;
   two or more nucleic acid sequences that encode two or more herpesvirus glycoprotein complex subunits or antigenic fragments thereof, wherein the two or more herpesvirus glycoprotein complex subunits or antigenic fragments thereof, when expressed by the expression system, form a herpesvirus glycoprotein complex;
   one or more 2A signal sequences between each of the two or more nucleic acid sequences;
   wherein the two or more herpesvirus glycoprotein complex subunits or antigenic fragments thereof of the first expression cassette and the two or more herpesvirus glycoprotein complex subunits or antigenic fragments thereof of the second expression cassette are simultaneously expressed by the expression system; and
   wherein the two or more herpesvirus glycoprotein complex subunits or antigenic fragments thereof of each expression cassette are derived from varicella-zoster virus (VZV), Epstein-Barr virus (EBV), Kaposi's Sarcoma-associated herpesvirus (KSHV), human herpesvirus 6 (HHV-6), human herpesvirus 7 (HHV-7).

3. The pharmaceutical composition of claim 1, wherein the one or more 2A signal sequence encode a 2A peptide of foot-and-mouth disease virus (F2A), a 2A peptide of equine rhinitis A virus (E2A), a 2A peptide of porcine teschovirus-1 (P2A), a 2A peptide of cytoplasmic polyhedrosis virus (BmCPV 2A), a 2A peptide of flacherie virus (BmIFV 2A), or a 2A peptide of Thosea asigna virus (T2A).

4. The pharmaceutical composition of claim 1, wherein the expression cassette further comprises a furin cleavage site upstream of each of the one or more 2A signal sequences.

5. The pharmaceutical composition of claim 1, wherein the promoter is a single promoter sequence located upstream of the subunits or the antigenic fragments thereof.

6. The pharmaceutical composition of claim 1, wherein the promoter is a vaccinia virus mH5 promoter, a pSyn promoter, a p7.5 promoter, or a p11 promoter.

7. The pharmaceutical composition of claim 1, wherein the two or more herpesvirus glycoprotein complex subunits include gD of HSV, gp350/220 of EBV, gpK8.1 of KSHV.

8. The pharmaceutical composition of claim 1, wherein the nucleic acid sequence encodes EBV EBNA1 or LMP2, or KSHV LANA, or other immunodominant antigens.

9. The pharmaceutical composition of claim 1, wherein the two or more nucleic acid sequences are naturally occurring DNA sequences.

10. The pharmaceutical composition of claim 1, wherein the two or more nucleic acid sequences are codon-optimized.

11. The pharmaceutical composition of claim 1, wherein the two or more nucleic acid sequences are DNA sequences.

12. The pharmaceutical composition of claim 1, wherein the vector is a modified vaccinia Ankara (MVA) vector.

13. A pharmaceutical composition comprising:
   (i) a first vector comprising a first expression cassette, the first expression cassette comprising:
      a first promoter, two or more nucleic acid sequences that encode two or more amino acids herpesvirus glycoprotein complex subunits or antigenic fragments thereof, and
      one or more 2A signal sequences between each of the two or more nucleic acid sequences,
      wherein the two or more herpesvirus glycoprotein complex subunits or antigenic fragments thereof, when expressed by the first expression cassette, form a herpesvirus glycoprotein complex;
      wherein the two or more herpesvirus glycoprotein complex subunits or antigenic fragments thereof are derived from varicella-zoster virus (VZV), Epstein-Barr virus (EBV), Kaposi's Sarcoma-associated herpesvirus (KSHV), human herpesvirus 6 (HHV-6), human herpesvirus 7 (HHV-7); and
      wherein the first vector is (i) a plasmid or (ii) a viral vector selected from a CMV vector, a vaccinia vector, or an adenoviral vector; and
   (ii) a second vector comprising a second expression cassette, the second expression cassette comprising:
      a second promoter, two or more nucleic acid sequences that encode two or more amino acids herpesvirus glycoprotein complex subunits or antigenic fragments thereof, and
      one or more 2A signal sequences between each of the two or more nucleic acid sequences, wherein the two or more herpesvirus glycoprotein complex subunits or antigenic fragments thereof, when expressed by the second expression cassette, form a herpesvirus glycoprotein complex;
      wherein the two or more herpesvirus glycoprotein complex subunits or antigenic fragments thereof are derived from varicella-zoster virus (VZV), Epstein-Barr virus (EBV), Kaposi's Sarcoma-associated herpesvirus (KSHV), human herpesvirus 6 (HHV-6), human herpesvirus 7 (HHV-7); and
      wherein the second vector is (i) a plasmid or (ii) a viral vector selected from a CMV vector, a vaccinia vector, or an adenoviral vector;

wherein the two or more herpesvirus glycoprotein complex subunits or antigenic fragments thereof of the first and second vectors are simultaneously expressed; and (iii) a pharmaceutically acceptable carrier, adjuvant, additive or combination thereof.

14. The pharmaceutical composition of claim 13, wherein the one or more 2A signal sequence encode a 2A peptide of foot-and-mouth disease virus (F2A), a 2A peptide of equine rhinitis A virus (E2A), a 2A peptide of porcine teschovirus-1 (P2A), a 2A peptide of cytoplasmic polyhedrosis virus (BmCPV 2A), a 2A peptide of flacherie virus (BmIFV 2A), or a 2A peptide of Thosea asigna virus (T2A).

15. The pharmaceutical composition of claim 13, wherein the expression cassette further comprises a furin cleavage site upstream of each of the one or more 2A signal sequences.

16. The pharmaceutical composition of claim 13, wherein the first promotor and/or the second promoter is a single promoter sequence located upstream of the subunits or the antigenic fragments thereof.

17. The pharmaceutical composition of claim 13, wherein the promoter is a vaccinia virus mH5 promoter, a pSyn promoter, a p7.5 promoter, or a p11 promoter.

18. The pharmaceutical composition of claim 13, wherein the two or more herpesvirus glycoprotein complex subunits include gD of HSV, gp350/220 of EBV, gpK8.1 of KSHV.

19. The pharmaceutical composition of claim 13, wherein the nucleic acid sequence encodes EBV EBNA1 or LMP2, or KSHV LANA, or other immunodominant antigens.

20. The pharmaceutical composition of claim 13, wherein the two or more nucleic acid sequences are DNA sequences.

21. The pharmaceutical composition of claim 13, wherein the vector is a modified vaccinia Ankara (MVA) vector.

* * * * *